US009519128B2

(12) United States Patent
Kaneko

(10) Patent No.: US 9,519,128 B2
(45) Date of Patent: Dec. 13, 2016

(54) IMAGE PROCESSING APPARATUS, MICROSCOPE SYSTEM, AND IMAGE PROCESSING METHOD

(71) Applicant: OLYMPUS CORPORATION, Tokyo (JP)

(72) Inventor: Yoshioki Kaneko, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 228 days.

(21) Appl. No.: 14/478,058

(22) Filed: Sep. 5, 2014

(65) Prior Publication Data

US 2014/0376087 A1 Dec. 25, 2014

Related U.S. Application Data

(63) Continuation of application No. PCT/JP2013/053869, filed on Feb. 18, 2013.

(30) Foreign Application Priority Data

Mar. 7, 2012 (JP) .................... 2012-051022

(51) Int. Cl.
  *G06K 9/00* (2006.01)
  *G02B 21/00* (2006.01)
  (Continued)

(52) U.S. Cl.
  CPC ......... *G02B 21/0076* (2013.01); *A61B 5/0071* (2013.01); *G01N 21/6458* (2013.01);
  (Continued)

(58) Field of Classification Search
  None
  See application file for complete search history.

(56) References Cited

U.S. PATENT DOCUMENTS 8,131,476 B2 3/2012 Cline et al.
2006/0252981 A1* 11/2006 Matsuda .................. B32B 7/02
  600/37

(Continued)

FOREIGN PATENT DOCUMENTS

JP 2003-102671 A 4/2003
JP 2010-500571 A 1/2010

(Continued)

OTHER PUBLICATIONS

International Search Report dated Mar. 19, 2013 issued in PCT/JP2013/053869.

(Continued)

*Primary Examiner* — Randolph I Chu
(74) *Attorney, Agent, or Firm* — Scully, Scott, Murphy & Presser, P.C.

(57) ABSTRACT

An image processing apparatus includes an image acquisition unit that acquires image information representing a fluorescence observation image of a specimen stained with hematoxylin-eosin, a spectrum generation unit that generates a plurality of spectra each representing a wavelength distribution of fluorescence intensity in a plurality of pixels in the fluorescence observation image, a pixel extraction unit that extracts at least two pixel groups with a feature of a particular spectrum from the plurality of pixels, and an image generation unit that generates an image based on the extracted pixel groups.

20 Claims, 36 Drawing Sheets

(51) Int. Cl.
*G01N 21/64* (2006.01)
*G02B 21/16* (2006.01)
*G02B 21/36* (2006.01)
*A61B 5/00* (2006.01)
*G02B 21/06* (2006.01)
*G02B 21/08* (2006.01)

(52) U.S. Cl.
CPC ............ *G02B 21/06* (2013.01); *G02B 21/16* (2013.01); *G02B 21/365* (2013.01); *G02B 21/088* (2013.01)

(56) References Cited

U.S. PATENT DOCUMENTS

| | | | |
|---|---|---|---|
| 2008/0194496 A1* | 8/2008 | Park | A61K 8/602 514/27 |
| 2011/0028331 A1* | 2/2011 | Milewicz | C12Q 1/6883 506/7 |
| 2012/0327211 A1 | 12/2012 | Yamamoto | |

FOREIGN PATENT DOCUMENTS

| | | |
|---|---|---|
| JP | 2011-002341 A | 1/2011 |
| JP | 2011-181015 A | 9/2011 |
| JP | 2012-022206 A | 2/2012 |

OTHER PUBLICATIONS

English Abstract of WO 2008/021677 A3, dated Feb. 21, 2008.
Apgar, J.M., "Fluorescence microscopy of rat embryo sections stained with haematoxylin-eosin and Masson's trichrome method", Journal of Microscopy (Jul. 1998), vol. 191, Pt. 1, pp. 20-27.

* cited by examiner

ELASTIC FIBER
BLOOD CORPUSCLE
CYTOPLASM

37 CALCULATION UNIT
371 PIXEL CLASSIFICATION UNIT
372 PIXEL EXTRACTION UNIT
353 IMAGE GENERATION UNIT

BLOOD CORPUSCLE    ELASTIC FIBER

ELASTIC FIBER

BLOOD CORPUSCLE

ELASTIC FIBER

BLOOD CORPUSCLE

OTHER TISSUES    ELASTIC FIBER

ELASTIC FIBER  BLOOD CORPUSCLE

↔ VASCULAR WALL THICKNESS

◄--► VESSEL DIAMETER

↔ AVERAGE VASCULAR WALL THICKNESS

◄--► MINIMUM VESSEL DIAMETER

| CIRCULARITY | RISK IN DISEASE CONDITION |
|---|---|
| 0-0.1 | 4 |
| 0.1-0.3 | 3 |
| 0.3-0.6 | 2 |
| 0.6-1.0 | 1 |

| VASCULAR WALL THICKNESS/VESSEL DIAMETER RATIO(%) | RISK IN DISEASE CONDITION |
|---|---|
| 60 OR MORE | 4 |
| 50 TO 60 | 3 |
| 40 TO 50 | 2 |
| 40 OR LESS | 1 |

| CIRCULARITY | ARTERIOSCLEROSIS RISK |
|---|---|
| 0-0.1 | 4 |
| 0.1-0.3 | 3 |
| 0.3-0.6 | 2 |
| 0.6-1.0 | 1 |

| VASCULAR WALL THICKNESS/VESSEL DIAMETER RATIO(%) | ARTERIOSCLEROSIS RISK |
|---|---|
| 60 OR MORE | 4 |
| 50 TO 60 | 3 |
| 40 TO 50 | 2 |
| 40 OR LESS | 1 |

FIG.38A

| CIRCULARITY | CANCER INFILTRATION RISK |
|---|---|
| 0-0.1 | 4 |
| 0.1-0.3 | 3 |
| 0.3-0.6 | 2 |
| 0.6-1.0 | 1 |

| VASCULAR WALL THICKNESS/VESSEL DIAMETER RATIO(%) | CANCER INFILTRATION RISK |
|---|---|
| 60 OR MORE | 4 |
| 50 TO 60 | 3 |
| 40 TO 50 | 2 |
| 40 OR LESS | 1 |

T32

| AREA OF REGION OF ELASTIC FIBER/CONTOUR LENGTH OF ELASTIC FIBER | ABNORMALITY |
|---|---|
| LESS THAN 1 | 5 |
| 1 TO 10 | 4 |
| 10 TO 100 | 3 |
| 100 TO 1000 | 2 |
| 1000 OR MORE | 0 |

IMAGE PROCESSING APPARATUS, MICROSCOPE SYSTEM, AND IMAGE PROCESSING METHOD

CROSS REFERENCES TO RELATED APPLICATIONS

This application is a continuation of PCT international application Ser. No. PCT/JP2013/053869 filed on Feb. 18, 2013 which designates the United States, incorporated herein by reference, and which claims the benefit of priority from Japanese Patent Application No. 2012-051022, filed on Mar. 7, 2012, incorporated herein by reference.

BACKGROUND

1. Technical Field

The disclosure relates to an image processing apparatus, a microscope system, and an image processing method for processing a microscope observation image of a biological specimen.

2. Related Art

Conventionally, observation of biological specimens with a microscope has been conducted by selecting the kind of staining or the microscopy depending on the observation target or observation purpose (for example, see JP 2011-2341 A). For example, as the morphological observation dye used for observing the morphology of the tissue or the cell, Hematoxylin-Eosin stain (hereinafter, "HE stain") which employs two pigments of hematoxylin and eosin, or non-fluorescent dye such as Papanicolaou stain (Pap dye) are known. The specimen stained with the morphology observation dye is generally subjected to bright-field observation using the transmission illumination with the use of an optical microscope.

In the pathological observation, staining called the specific staining or immunostaining may be conducted for compensating the lack of data in the morphological diagnosis based on the morphology information or for determining whether medicine administration is appropriate or not. For example, in the case of conducting the molecular pathological examination for diagnosing the functional abnormality such as the expression abnormality of a target molecule (particular gene or protein), the target molecule may be subjected to the fluorescence observation with the epi-illumination after the target molecule is marked (stained) with the fluorescence by the IHC (immunohistochemistry) method, the ICC (immunocytochemistry) method, the ISH (in-situ hybridization) method or the like, or subjected to the bright-field observation after the target molecule is marked with an enzyme.

The specific staining or immunostaining as above, however, require time and effort in preparing the specimen, which also increases the cost. For these reasons, a method has been examined in which the target tissue is observed without the use of such staining.

JP 2003-102671 A discloses an endoscope system for irradiating a biological tissue with a UV ray and detecting autofluorescence of the elastic fiber caused by the irradiation.

SUMMARY

In accordance with some embodiments, an image processing apparatus, a microscope system, and an image processing method for processing a microscope observation image of a biological specimen are presented.

In some embodiments, an image processing apparatus includes: an image acquisition unit that acquires image information representing a fluorescence observation image of a specimen stained with hematoxylin-eosin; a spectrum generation unit that generates a plurality of spectra each representing a wavelength distribution of fluorescence intensity in a plurality of pixels in the fluorescence observation image; a pixel extraction unit that extracts at least two pixel groups with a feature of a particular spectrum from the plurality of pixels; and an image generation unit that generates an image based on the extracted pixel groups.

In some embodiments, a microscope system includes: the above-mentioned image processing apparatus; a stage on which the specimen is configured to be placed; an epi-illumination optical system that emits excitation light toward the stage; an objective optical system that is provided to face the stage and receives light from a direction of the specimen; a filter that extracts fluorescence light from the light transmitted through the objective optical system; and an imaging unit that is provided on an optical path of the light transmitted through the objective optical system and generates image information by capturing an observation image of the specimen.

In some embodiments, an image processing method includes: acquiring image information representing a fluorescence observation image of a specimen stained with hematoxylin-eosin; generating a plurality of spectra each representing a wavelength distribution of fluorescence intensity in a plurality of pixels in the fluorescence observation image; extracting at least two pixel groups with a feature of a particular spectrum from the plurality of pixels; and generating an image based on the extracted pixel groups.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 36A is a lookup table in which the circularity of the elastic fiber and the risk in disease condition are correlated to each other;

FIG. 36B is a lookup table in which the vascular wall thickness/vessel diameter ratio and the risk in disease condition are correlated to each other;

FIG. 37A is a lookup table in which the circularity of the elastic fiber and the arteriosclerosis risk are correlated to each other;

FIG. 37B is a lookup table in which the vascular wall thickness/vessel diameter ratio and the arteriosclerosis risk are correlated to each other;

FIG. 38A is a lookup table in which the circularity of the elastic fiber and the cancer infiltration risk are correlated to each other;

FIG. 38B is a lookup table in which the vascular wall thickness/vessel diameter ratio and the cancer infiltration risk are correlated to each other;

DETAILED DESCRIPTION

Figure 1:
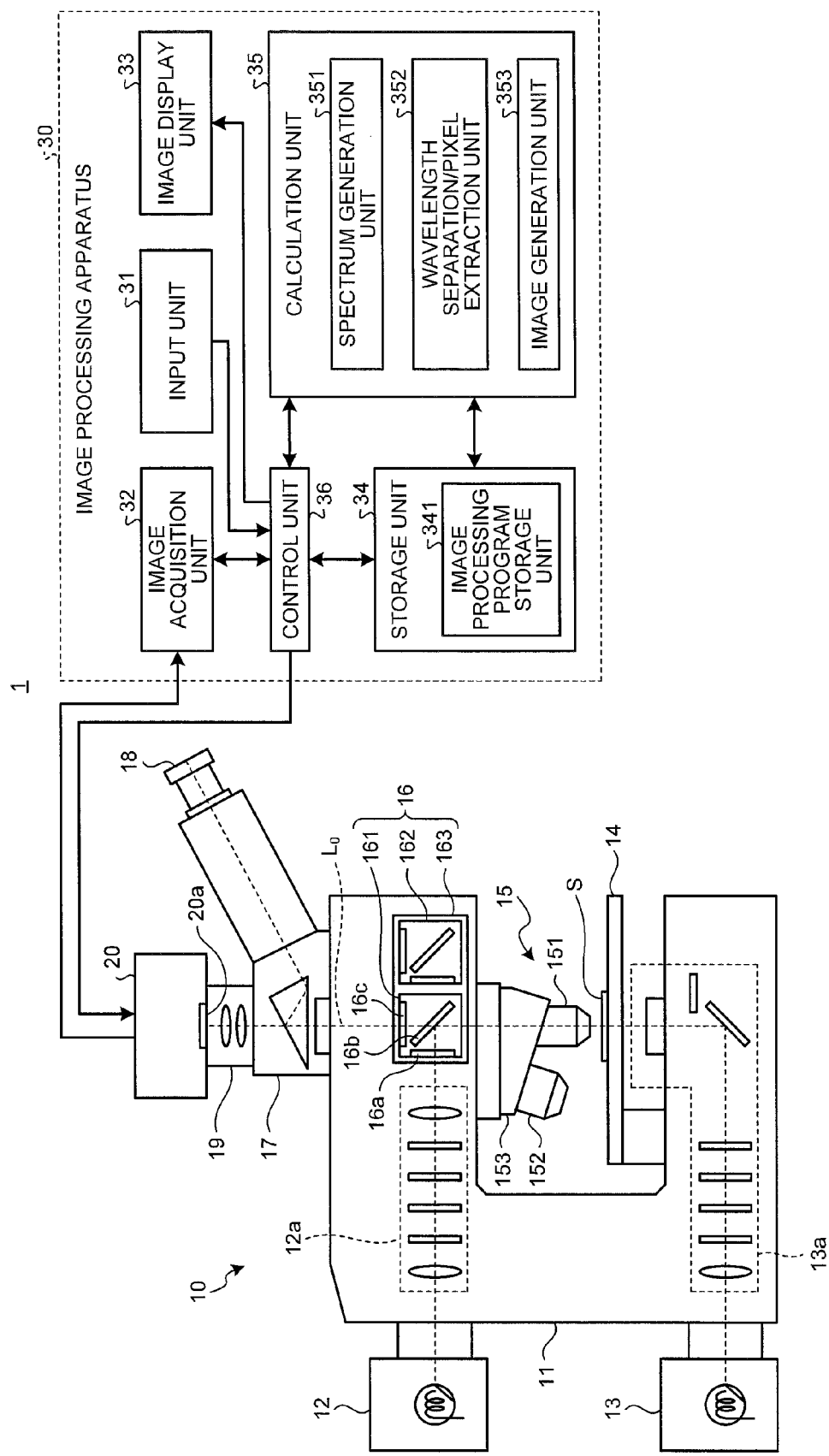
FIG. 1 is a diagram illustrating a structure of a microscope system according to a first embodiment of the present invention.

Embodiments of an image processing apparatus, a microscope system, and an image processing method according to the present invention will be described below in detail with reference to the drawings. Note that the present invention is not limited by the embodiments. In the description of each drawing, the same reference numerals are used to refer to the same elements.

First Embodiment

FIG. 1 is a diagram illustrating a structure of a microscope system according to a first embodiment of the present invention. As illustrated in FIG. 1, a microscope system 1 according to the first embodiment includes a microscope device 10, and an image processing apparatus 30 for processing an image of a specimen (microscope observation image) observed in the microscope device 10.

The microscope device 10 includes an arm portion 11 with a shape like a letter of C, an epi-illumination light source 12 and an epi-illumination optical system 12a provided for the arm portion 11, a transmission illumination light source 13 and a transmission illumination optical system 13a, a specimen stage 14 provided for the arm portion 11, an objective lens unit 15 including an objective lens 151 disposed to face the specimen stage 14 on an observation optical path $L_0$, a cube unit 16 provided on the observation optical path $L_0$, a trinocular tube unit 17 provided on the observation optical path $L_0$, an eyepiece unit 18 provided through the trinocular tube unit 17, and a tube lens unit 19 connected to the trinocular tube unit 17. The tube lens unit 19 has an end thereof provided with an imaging unit 20.

The epi-illumination optical system 12a includes various optical members (such as a filter unit, a shutter, an aperture diaphragm, and an aperture stop) that condense the epi-illumination light emitted from the epi-illumination light source 12 and guide the light in a direction to the observation optical path $L_0$. On the other hand, the transmission illumination optical system 13a includes various optical members (such as a collector lens, a filter unit, an aperture diaphragm, a shutter, an aperture stop, a condenser optical element unit, and a top lens unit) that condense the transmission illumination light emitted from the transmission illumination light source 13 and guide the light in a direction to the observation optical path $L_0$.

The objective lens unit 15 includes a plurality of objective lenses 151 and 152 with different magnifications, and a revolver 153 for holding these objective lenses 151 and 152. By rotating the revolver 153 to switch the objective lenses 151 and 152 to be disposed to face the specimen stage 14 on the observation optical path $L_0$, the magnification of the microscope observation image can be changed. In FIG. 1, the objective lens 151 is disposed on the observation optical path $L_0$.

The cube unit 16 includes a plurality of optical cubes 161 and 162, and a cube switching unit 163 that holds the optical cubes 161 and 162 in a manner that the cubes 161 and 162 can be switched, and the cube unit 16 switches the optical cubes 161 and 162 to be disposed on the observation optical path $L_0$ depending on the microscopy. For example, in the case of conducting the fluorescence observation in the microscope device 10, an optical cube (fluorescence cube) 161 formed by combining the following in a cube shape is used: an excitation filter 16a that selectively transmits the light (excitation light) with a particular wavelength band among the light emitted from the epi-illumination light source 12 and transmitted through the epi-illumination optical system 12a; a dichroic mirror 16b that reflects the excitation light selected by the excitation filter 16a and transmits the fluorescence generated in the specimen S; and an absorption filter 16c that selectively transmits only the light (fluorescence light) with a particular wavelength range among the light entering from a direction of the specimen S. Note that in the case of conducting the transmission bright-field observation in the microscope device 10, the cube switching unit 163 moves the optical cubes 161 and 162 to a position deviated from the observation optical path $L_0$.

The trinocular tube unit 17 branches the observation light (transmission light or fluorescence light) of the specimen S entered from a direction of the objective lens 151 into a direction of the eyepiece unit 18 and a direction of the tube lens unit 19. The eyepiece unit 18 is used when a user directly observes the specimen S.

The tube lens unit 19 includes a zoom unit including a plurality of zoom lenses and a driving unit (not shown) for changing the positions of these zoom lenses. The zoom unit expands or contracts the image to be captured in the imaging field by adjusting the positions of the zoom lenses.

The imaging unit 20 includes an imaging element such as a CCD, and is formed of a multiband camera capable of capturing a color image having pixel levels (pixel values) in a plurality of wavelength ranges (bands) different among pixels. In the first embodiment, the imaging unit 20 is a multiband camera capable of imaging in at least three bands in approximately 400 nm to 900 nm, which is the range from the visible region to the near-infrared region. Note that the imaging wavelength band at the actual imaging of the imaging unit 20 may be changed as appropriate depending on the kind of the pigment for staining the specimen or the fluorescent cube.

The imaging unit 20 has a light reception surface 20a for receiving the observation light emitted from the objective lens 151 and traveling through the tube lens unit 19, generates image data by converting the observation light having entered the light reception surface 20a into an electric signal, and then outputs the image data to the image processing apparatus 30.

The operation of the imaging unit 20 including the timing of operating the units of the above microscope device 10, the imaging timing, the exposure time, and the change of the imaging wavelength band may be controllable by the image processing apparatus 30.

The image processing apparatus 30 includes an input unit 31 that accepts the input of information or instruction to the image processing apparatus 30, an image acquisition unit 32 as the interface that accepts the input of the image data output from the imaging unit 20, an image display unit 33 displaying the microscope image or other pieces of information, a storage unit 34, a calculation unit 35 for performing a specified image process on the microscope image, and a control unit 36 for controlling the operation of the above units and the operation of the imaging unit 20.

The input unit 31 includes an input device such as a keyboard, various buttons, or various switches, or a pointing device such as a mouse or a touch panel, and inputs a signal according to the operation of the user through such a device to the control unit 36.

The image acquisition unit 32 acquires from the imaging unit 20, the image data representing the microscope image (hereinafter referred to as a fluorescence observation image) generated from the fluorescence observation by irradiating the specimen S with the epi-illumination light, or the image data representing the microscope image (hereinafter referred to as a bright-field observation image) generated from the bright-field observation by irradiating the specimen S with the transmission illumination light.

The image display unit 33 includes, for example, a display device such as an LCD, an EL display, or a CRT display, and displays various kinds of screens on which various pieces of information or microscope images are disposed in a specified format in accordance with a control signal output from the control unit 36.

The storage unit 34 includes a semiconductor memory such as a flash memory whose data can be updated and in which data can be recorded, a RAM, or a ROM, a hard disk incorporated or connected via a data communication terminal, a recording medium such as an MO, a CD-R, or a DVD-R, or a reader for reading out the information recorded in the recording medium. In the storage unit 34, the image data output from the imaging unit 20, various pieces of setting information or programs to be executed by the calculation unit 35 or the control unit 36 are recorded. Specifically, the storage unit 34 includes an image processing program storage unit 341 that stores the image processing program for generating the image from which a particular specimen component is extracted on the basis of the intensity of the fluorescent light in the fluorescence observation image (hereinafter the intensity is referred to as fluorescence intensity). The specimen component herein refers to various kinds of elements constituting the specimen S and includes, for example, the tissues constituting the biological body such as an elastic fiber or a collagenous fiber, a blood corpuscle (blood cell such as red corpuscle, white corpuscle (neutrophil, eosinophil, basophil, lymphocyte, monocyte), or thrombocyte), and a structure constituting a cell such as a cell membrane or a cell nucleus. The storage unit 34 stores standard data (for example, data of fluorescence intensity spectrum to be described below) that are acquired in advance in regard to the specimen component as the various kinds of data used in the execution of the image processing program stored in the image processing program storage unit 341.

The calculation unit 35 includes a hardware device such as a CPU, and executes the image processing for generating the image from which the particular specimen component is extracted, on the basis of the fluorescence intensity of the fluorescence observation image of the specimen S that has been stained for the purpose of the bright-field observation, for example with the HE stain, with reference to the image data stored in the storage unit 34 by reading in the image processing program stored in the image processing program storage unit 341.

More specifically, the calculation unit 35 includes a spectrum generation unit 351 that acquires the wavelength distribution of the fluorescence intensity across a plurality of pixels within the fluorescence observation image (hereinafter the distribution is referred to as the fluorescence intensity spectrum) on the basis of the image data acquired by the image acquisition unit 32, a wavelength separation/pixel extraction unit 352 that extracts a pixel group having the characteristic of a particular fluorescence intensity spectrum from among the plurality of pixels on the basis of the fluorescence intensity spectrum of each pixel, and an image generation unit 353 that generates an image based on the image data acquired by the image acquisition unit 32 or the image data corresponding to the pixel group extracted by the wavelength separation/pixel extraction unit 352.

The control unit 36 includes a hardware device such as a CPU, and instructs each unit of the image processing apparatus 30 or transfers the data to the unit in accordance with the operation signal and the like input from the input unit 31 by reading in various programs stored in the storage unit 34, thereby controlling the operation of the entire image processing apparatus 30 generally.

Figure 2:
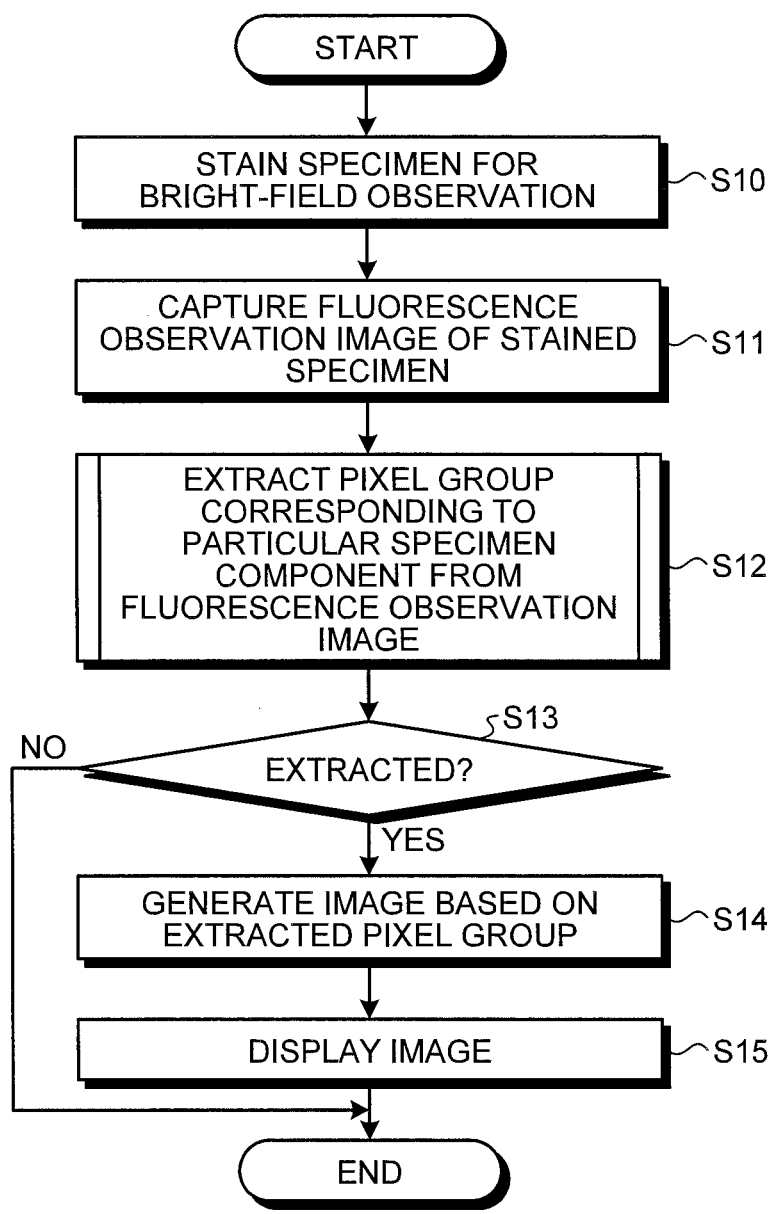
FIG. 2 is a flowchart illustrating a specimen observation method according to the first embodiment of the present invention.

Next, an image processing method according to the first embodiment is described. FIG. 2 is a flowchart illustrating a specimen observation method including the image processing method according to the first embodiment.

Figure 3:
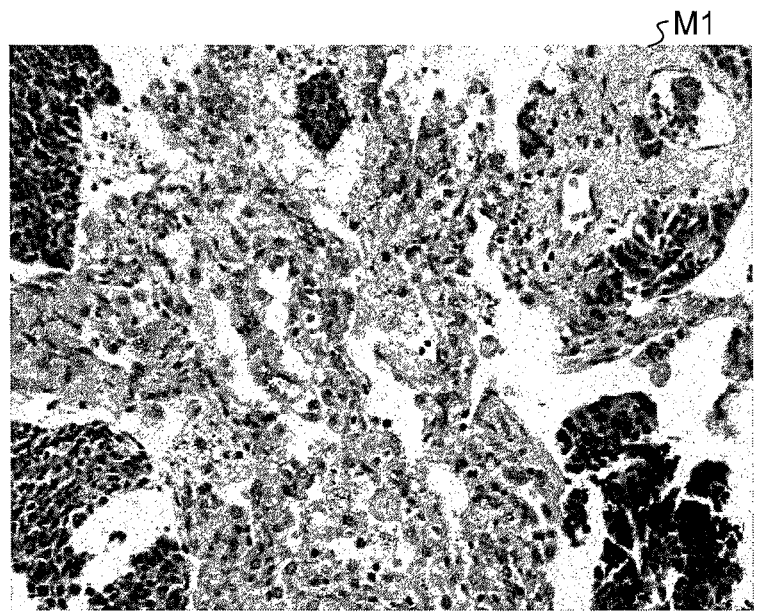
FIG. 3 is a photograph representing an example of a bright-field observation image of a specimen stained with HE.

First, in Step S10, the specimen S as the observation target is stained for the bright-field observation. The specimen is stained with HE in the first embodiment. An image M1 illustrated in FIG. 3 is an image of an example of the specimen S observed with a microscope, the image being obtained by staining the specimen, which is a paraffin section of a human lung fixed on a slide glass, with the HE stain. Note that the specimen that has been stained with HE is generally subjected to the transmission bright-field observation; therefore, FIG. 3 illustrates the bright-field observation image.

In the subsequent Step S11, the microscope system 1 captures the fluorescence observation image of the stained specimen S. More specifically, the microscope system 1 illuminates the specimen S from the epi-illumination light source 12 and the epi-illumination optical system 12a in the state that the optical cube 161 for the fluorescence observation is disposed in the observation optical path $L_O$ of the microscope device 10. Thus, the specimen S is irradiated with the excitation light with a specified wavelength component having transmitted through the optical cube 161, thereby exciting the particular specimen component in the specimen S to generate the fluorescence light. This fluorescence light transmits through the objective lens 151 and the optical cube 161 and the like along the observation optical path $L_O$ and enters the light reception surface 20a of the imaging unit 20. The imaging unit 20 captures the observation image of the specimen S that is represented by the fluorescence light with a plurality of bands, and outputs the image data of each band to the image processing apparatus 30. These pieces of image data are input to the image processing apparatus 30 through the image acquisition unit 32 and stored in the storage unit 34.

In the case of capturing the fluorescence observation image of the HE-stained specimen, such a fluorescent cube is preferably used that selects the excitation light in the UV region around 300 nm to 400 nm and reflects the light toward the specimen S and moreover selects the fluorescence light around 520 nm to 650 nm and transmits the light toward the imaging unit 20.

Figure 4:
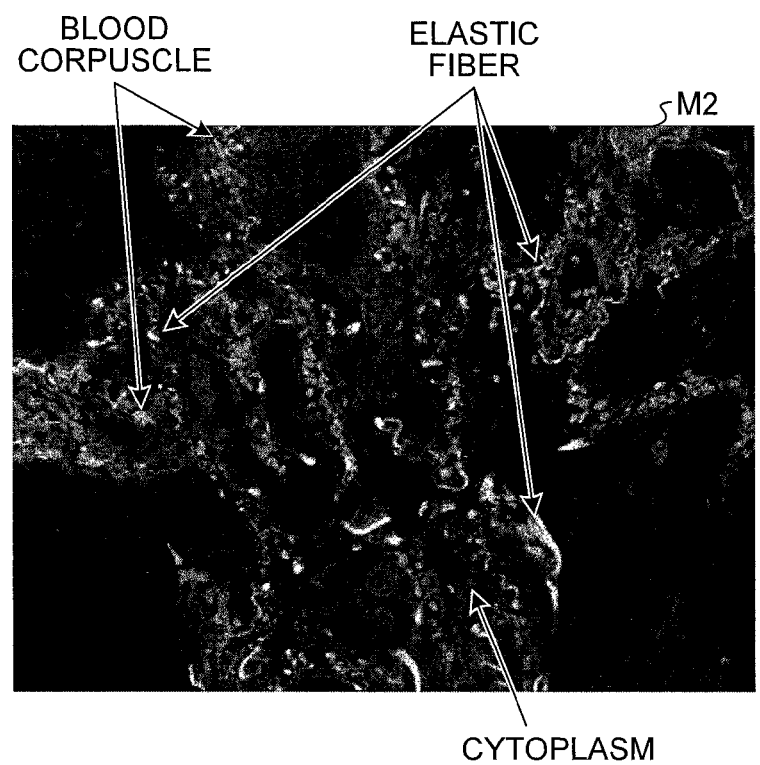
FIG. 4 is a photograph representing an example of a fluorescence observation image of the same specimen as that in FIG. 3.

FIG. 4 is the fluorescence observation image acquired by observing the same specimen as the image M1 illustrated in FIG. 3 with the fluorescence through the fluorescence cube U-MWU manufactured by OLYMPUS Corp. The region with the high fluorescence intensity in the fluorescence observation image M2 represents the elastic fiber (yellow-greenish) and the blood corpuscle (orange) among the specimen components. Moreover, the region of a cytoplasm (greenish) can be observed though the fluorescence intensity thereof is lower than that of the elastic fiber and the blood corpuscle.

Figure 5:
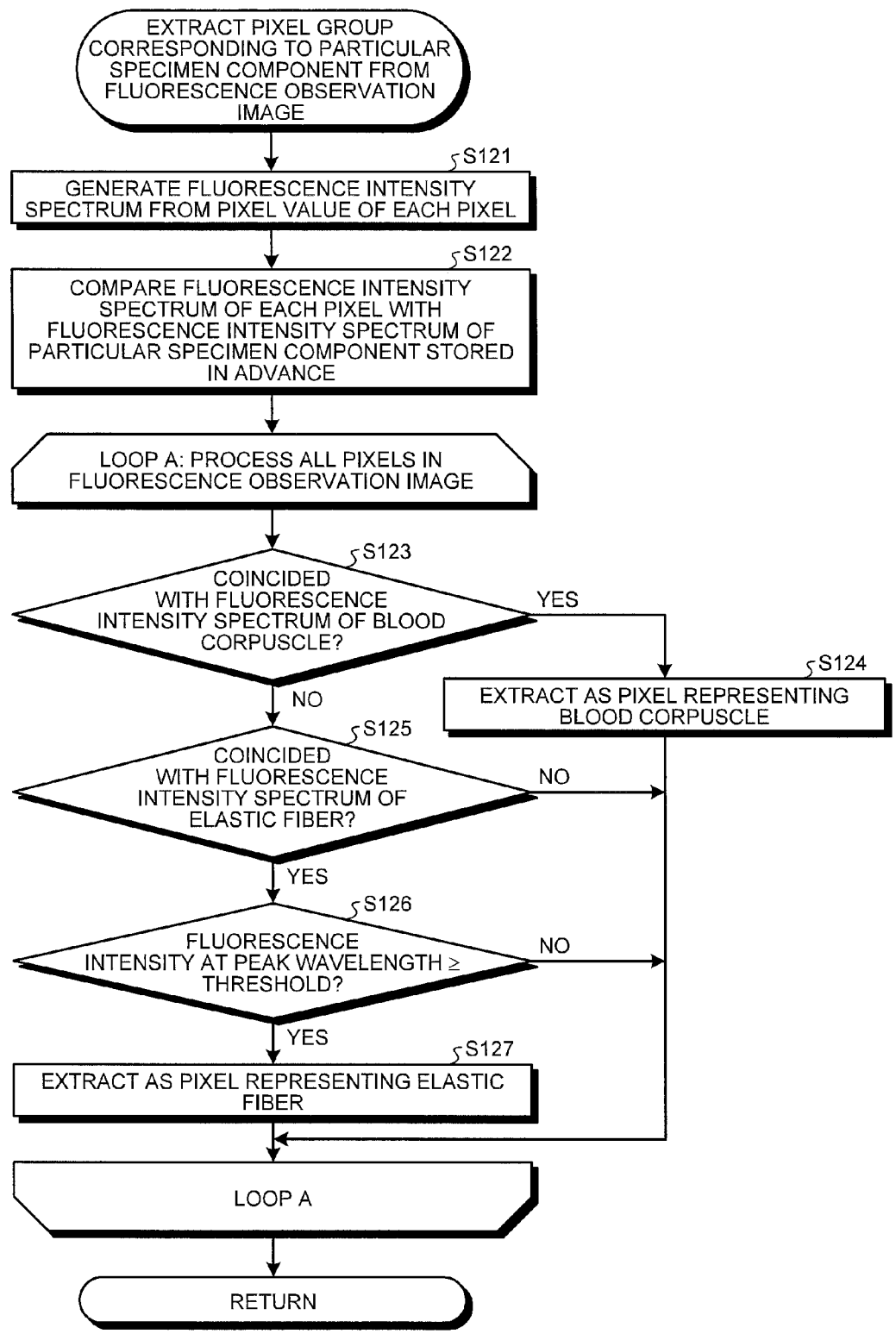
FIG. 5 is a flowchart illustrating the process for extracting a pixel group corresponding to the particular specimen component from the fluorescence observation image.

In the subsequent Step S12, the image processing apparatus 30 executes the process of reading out the image data of the fluorescence observation image captured in Step S11 out of the storage unit 34 and extracting the pixel group corresponding to the particular specimen component from the fluorescence observation image. FIG. 5 is a flowchart illustrating the process for extracting the pixel group corresponding to the particular specimen component from the fluorescence observation image.

In Step S121 of FIG. 5, the spectrum generation unit 351 generates the fluorescence intensity spectrum from the pixel value of each pixel in the fluorescence observation image. Specifically, the pixel value in each band of the image data may be acquired.

In the subsequent Step S122, the wavelength separation/pixel extraction unit 352 reads out the data representing the fluorescence intensity spectrum of the particular specimen component that is stored in advance in the storage unit 34, and compares the fluorescence intensity spectrum of each pixel generated in Step S121 with the fluorescence intensity spectrum read out from the storage unit 34. Description is hereinafter made of the blood corpuscle and the elastic fiber as the examples of the particular specimen component.

Figure 6:
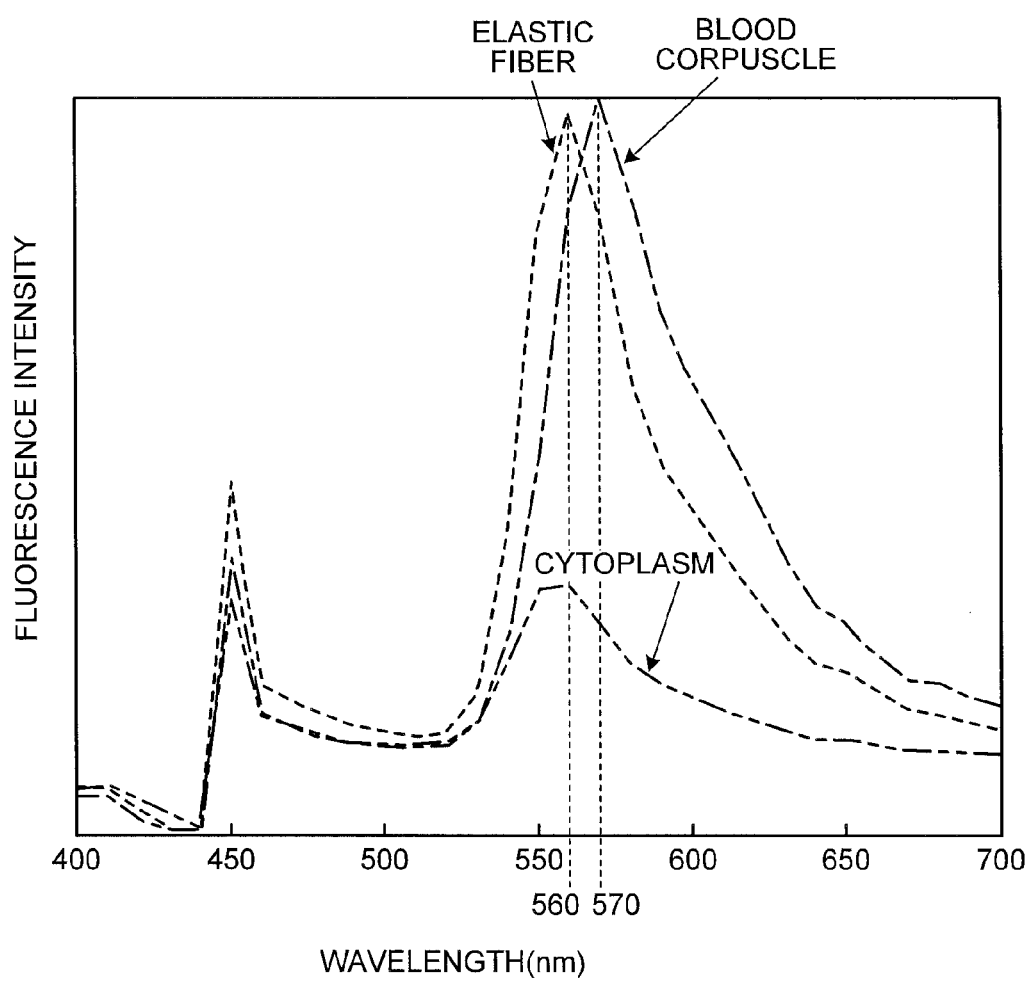
FIG. 6 is a graph representing a part of the fluorescence intensity spectrum in the fluorescence observation image illustrated in FIG. 4.

FIG. 6 is a graph of an example of the fluorescence intensity spectrum read out from the storage unit 34. Each curve in FIG. 6 represents the standard spectrum of the fluorescence emitted from the regions of the blood corpuscle, the elastic fiber, and the cytoplasm when the HE-stained specimen is irradiated with a UV ray with a wavelength around 300 nm to 400 nm. Among these, the spectrum waveform of the blood corpuscle has a maximum peak wavelength around 570 nm. The spectrum waveform of the elastic fiber has a maximum peak wavelength around 560 nm. The spectrum wavelength of the cytoplasm has a maximum peak wavelength around 560 nm, which is similar to the elastic fiber; however, the fluorescence intensity thereof is lower than that of the elastic fiber as a whole.

Subsequently, the wavelength separation/pixel extraction unit 352 executes the process of a loop A for all the pixels in the fluorescence observation image. In Step S123, the wavelength separation/pixel extraction unit 352 determines whether the fluorescence intensity spectrum of the pixel to be processed coincides with the fluorescence intensity spectrum of the blood corpuscle. This determination is made based on the peak wavelength and the waveform of the fluorescence intensity spectrum.

If the fluorescence intensity spectrum of the pixel to be processed coincides with the fluorescence intensity spectrum of the blood corpuscle (Yes in Step S123), the wavelength separation/pixel extraction unit 352 extracts the pixel to be processed as the pixel representing the blood corpuscle (Step S124). After that, the operation of the wavelength separation/pixel extraction unit 352 transits to the process for the pixel to be processed next.

On the other hand, if the fluorescence intensity spectrum of the pixel to be processed does not coincide with the fluorescence intensity spectrum of the blood corpuscle (No in Step S123), the wavelength separation/pixel extraction unit 352 determines whether the fluorescence intensity spectrum of the pixel coincides with the fluorescence intensity spectrum of the elastic fiber (Step S125). This determination is also made based on the peak wavelength and the waveform of the fluorescence intensity spectrum.

If the fluorescence intensity spectrum of the pixel does not coincide with the fluorescence intensity spectrum of the elastic fiber (No in Step S125), the wavelength separation/pixel extraction unit 352 does not extract the pixel and transits to the process for the pixel to be processed next.

If the fluorescence intensity spectrum of the pixel coincides with the fluorescence intensity spectrum of the elastic fiber (Yes in Step S125), the wavelength separation/pixel extraction unit 352 further determines whether the fluorescence intensity at the peak wavelength of the pixel (pixel value) is greater than or equal to the specified threshold (Step S126). Here, as illustrated in FIG. 6, the cytoplasm has the same peak wavelength as the peak wavelength (560 nm) of the elastic fiber; however, the fluorescence intensity at the peak wavelength of the cytoplasm is much lower than that of the elastic fiber (for example, less than or equal to a half of the intensity of the elastic fiber). Therefore, the wavelength separation/pixel extraction unit 352 separates the elastic fiber region and the cytoplasm region on the basis of the fluorescence intensity at the peak wavelength.

If the fluorescence intensity at the peak wavelength of the pixel is greater than or equal to the threshold (Yes in Step S126), the wavelength separation/pixel extraction unit 352 extracts the pixel as the pixel representing the elastic fiber (Step S127).

On the other hand, if the fluorescence intensity at the peak wavelength of the pixel is less than the threshold (No in Step S126), the wavelength separation/pixel extraction unit 352 does not extract the pixel and transits to the process for the pixel to be processed next. Note that the wavelength separation/pixel extraction unit 352 may extract the pixel as the pixel representing the cytoplasm separate from the elastic fiber.

Upon the end of the process of the loop A for all the pixels in the fluorescence observation image, the process returns to the main routine.

In Step S13 subsequent to Step S12, the calculation unit 35 determines whether the pixel group corresponding to the particular specimen component has been extracted or not. If the pixel group has been extracted (Yes in Step S13), the image generation unit 353 generates an image based on the extracted pixel group (hereinafter referred to as extraction image) (Step S14). On this occasion, in the case where a plurality of pixel groups has been extracted in Step S13, the image generation unit 353 may generate the image for each pixel group or may generate the image using all of the extracted pixel groups. The image generation unit 353 may distinguish the particular specimen component in the extraction image by allocating different colors among the pixel groups.

Figure 7:
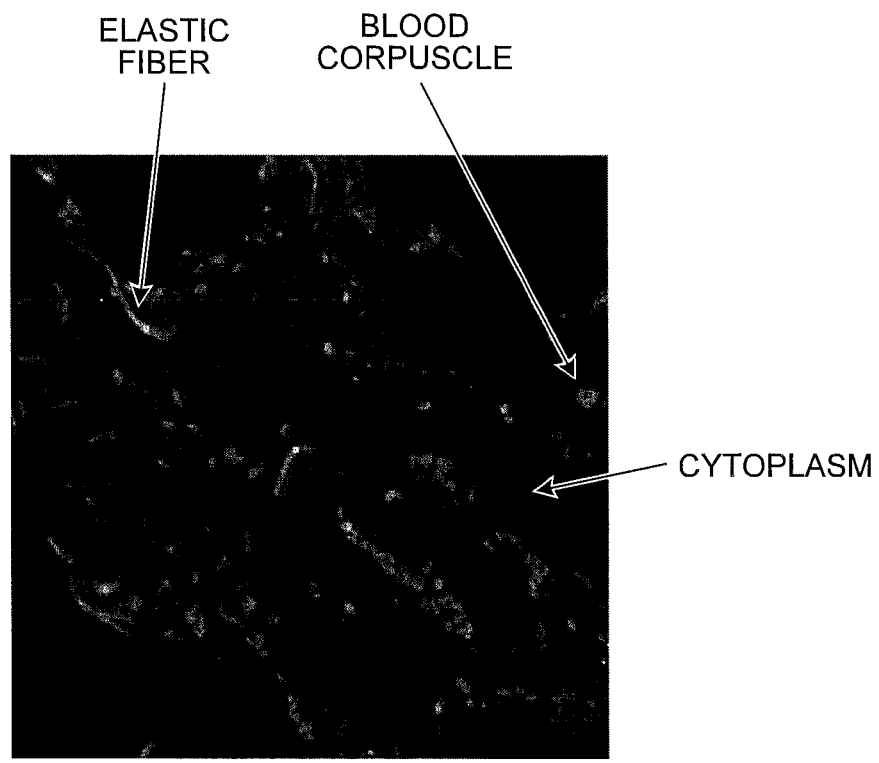
FIG. 7 is an example of displaying the extraction image representing the elastic fiber and the blood corpuscle extracted from the fluorescence observation image illustrated in FIG. 4.

In the subsequent Step S15, the control unit 36 displays the generated extraction image on the image display unit 33. FIG. 7 is an example of displaying the extraction image representing the elastic fiber and the blood corpuscle extracted from the fluorescence observation image illustrated in FIG. 4. In FIG. 7, the cytoplasm region which has been extracted separate from the pixel representing the elastic fiber is also shown as a reference.

On the other hand, if the pixel group corresponding to the particular specimen component has not been extracted (No in Step S13), the process ends.

As described above, according to the first embodiment, the specimen component that generates the autofluorescence can be extracted simply, accurately, and stably from the fluorescence observation image of the specimen stained for the bright-field observation. On this occasion, the fluorescence intensity spectrum of each pixel in the fluorescence observation image is compared with the fluorescence intensity spectrum of the particular specimen component that is stored in advance and the pixel group representing each specimen component is separately extracted. Thus, the specimen component that generates the autofluorescence can be analyzed quantitatively and the analysis can be made specifically, precisely, and objectively.

In particular, according to the first embodiment, the elastic fiber that has conventionally been observed just by the specific staining can be observed after being extracted from the image easily without wasting the time and effort. On this occasion, the blood corpuscle from which the information would be lost in the specific staining for observing the elastic fiber can be extracted separate from the elastic fiber. Therefore, according to the first embodiment, both the elastic fiber and the blood corpuscle can be subjected to the correct analysis or the comparative observation.

In addition, the specimen components that generate the autofluorescence can be separately extracted for each kind according to the first embodiment; therefore, the extracted plural kinds of specimen components can be displayed separately or be displayed collectively. In other words, the specimen components can be displayed in various formats; therefore, the image diagnosis can be conducted in a wider range.

Moreover, in the first embodiment, the specimen S can be captured using the multiband camera; therefore, the spectrum information according to the number of bands can be acquired from the fluorescence observation image and the autofluorescence can be separately extracted easily.

First Modified Example

Figure 8:
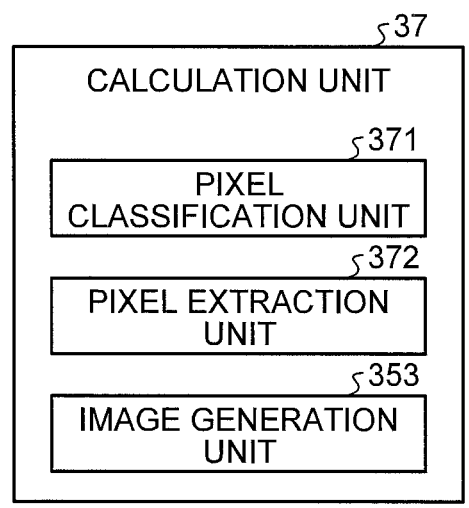
FIG. 8 is a block diagram illustrating a structure of a calculation unit according to a first modified example.

Next, a first modified example of the first embodiment is described. FIG. 8 is a block diagram illustrating a structure of a calculation unit according to the first modified example. The microscope system 1 according to the first modified example includes a calculation unit 37 illustrated in FIG. 8 instead of the calculation unit 35 illustrated in FIG. 1. Note that the structure of each unit of the microscope system other than the calculation unit 37 is similar to that of the first embodiment.

The calculation unit 37 includes a pixel classification unit 371 and a pixel extraction unit 372 instead of the spectrum generation unit 351 and the wavelength separation/pixel extraction unit 352 illustrated in FIG. 1. The operation of the calculation unit 37 is described below.

The pixel classification unit 371 acquires the image data representing the fluorescence observation image captured at each of three bands of R, G, and B from the specimen S stained for the bright-field observation, and acquires the pixel values (R value, G value, and B value) of the pixels of the fluorescence observation image from the image data. Subsequently, the pixel classification unit 371 maps these pixel values in the RGB space to create the pixel value distribution in the RGB space. The pixel classification unit 371 clusters this pixel value distribution to classify the pixels in the fluorescence observation image into a plurality of classes according to the pixel value.

The pixel extraction unit 372 extracts the pixel group for each class. The pixel group for each class corresponds to the region of each specimen component in the fluorescence observation image. In this case, the image generation unit 353 generates the image on the basis of the pixel group extracted by the pixel extraction unit 372.

According to the first modified example described above, the pixels in the fluorescence observation image are extracted for each class in the RGB space; therefore, it becomes possible to classify the specimen components according to the color of the autofluorescence. Thus, the state of each specimen component can be correctly known.

Second Embodiment

Figure 9:
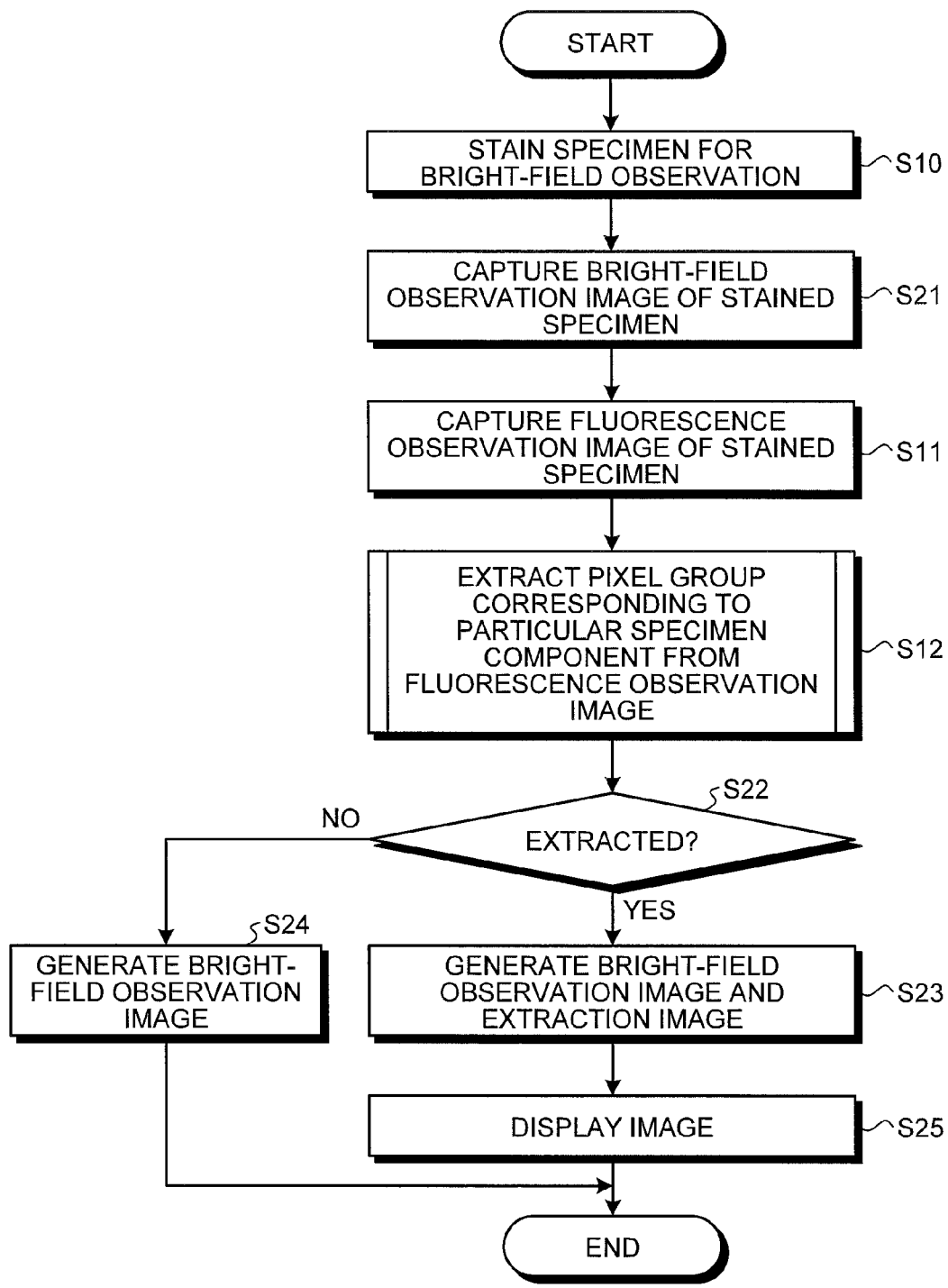
FIG. 9 is a flowchart illustrating a specimen observation method according to a second embodiment of the present invention.

A second embodiment of the present invention is described next. FIG. 9 is a flowchart illustrating a specimen observation method including an image processing method according to the second embodiment. Note that the process in Steps S10, S11, and S12 illustrated in FIG. 9 is common to the process in the first embodiment. The structure of a microscope system according to the second embodiment is similar to that of FIG. 1.

In Step S21 subsequent to Step S10, in the microscope system 1, the specimen S stained for the bright-field observation (for example, with the HE stain) is placed on the specimen stage 14 and the specimen S is irradiated from the transmission illumination light source 13 and the transmission illumination optical system 13a; thus, the bright-field observation image of the specimen S is captured. Note that, on this occasion, the optical cube 161 is absent in the observation optical path $L_O$ of the microscope device 10. The image data created in the imaging unit 20 are input to the image processing apparatus 30 through the image acquisition unit 32 and stored in the storage unit 34.

In Step S22 subsequent to Step S12, the calculation unit 35 determines whether the pixel group corresponding to the particular specimen component has been extracted or not. If the pixel group has been extracted (Yes in Step S22), the image generation unit 353 generates the bright-field observation image by reading out from the storage unit 34 the image data generated by the capture in Step S21 and moreover generates the extraction image based on the pixel group extracted in Step S12 (Step S23). On this occasion, if a plurality of pixel groups has been extracted in Step S12, the image generation unit 353 may generate the extraction image for each pixel group or may generate the extraction image based on all of the extracted pixel groups.

On the other hand, if the pixel group corresponding to the particular specimen component has not been extracted (No in Step S22), the image generation unit 353 generates only the bright-field observation image (Step S24).

In Step S25, the control unit 36 displays the bright-field observation image and/or the extraction image generated by the image generation unit 353 on the image display unit 33.

Figure 10:
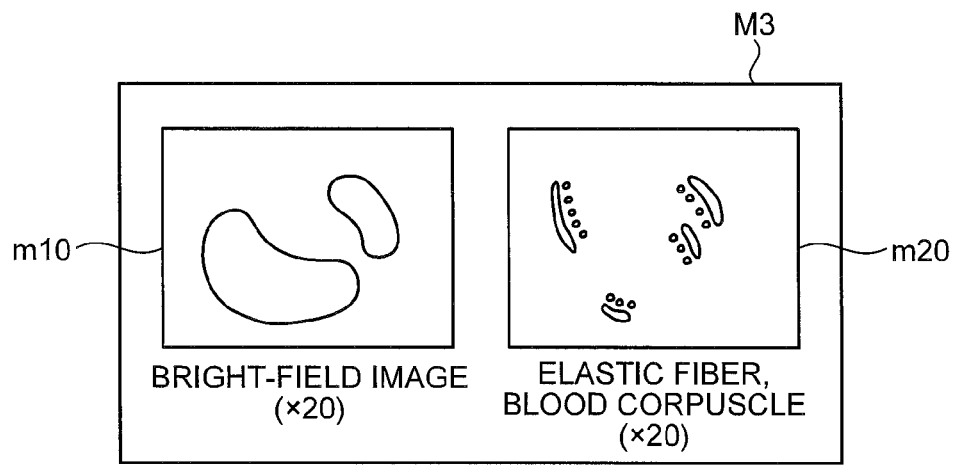
FIG. 10 is a schematic diagram illustrating an example of displaying the bright-field observation image and the extraction image in the second embodiment.

FIG. 10 is a schematic diagram illustrating an example of displaying the bright-field observation image and the extraction image. In the case of displaying a bright-field observation image m10 and an extraction image m20 on one screen M3, the positions of the bright-field observation image m10 and the extraction image m20 are not particularly limited; however, the bright-field observation image m10 and the extraction image m20 are preferably arranged side by side horizontally or vertically at the same magnification to allow a user to observe the bright-field observation image m10 and the extraction image m20 while comparing the both. In the case where the plural extraction images (for example, the extraction image of the elastic fiber and the extraction image of the blood corpuscle) are generated, the bright-field observation image and the plural extraction images may be displayed on one screen or the extraction image to be displayed with the bright-field observation image may be selected by a user.

As thus described, since the bright-field observation image of the specimen S and the extraction images extracted from the fluorescence observation image are displayed at the same time according to the second embodiment, the user can observe the entire image of the specimen S and the particular specimen component in the specimen S while comparing the both.

Second Modified Example

Next, a second modified example of the second embodiment is described. In the second embodiment, the fluorescence observation image is captured by the epi-illumination through the epi-illumination optical system 12a provided for the microscope device 10, and the bright-field observation image is captured by the transmission illumination through the transmission illumination optical system 13a. However, the fluorescence observation image of the specimen S may be captured by performing the illumination for the dark-field observation by inserting the excitation filter and the dark-field condenser to the transmission illumination optical system 13a. In this case, both the bright-field observation image and the fluorescence observation image can be acquired using the microscope device including the transmission illumination optical system only. Therefore, the image analysis for the specimen S can be conducted with the inexpensive device structure.

Third Embodiment

Figure 11:
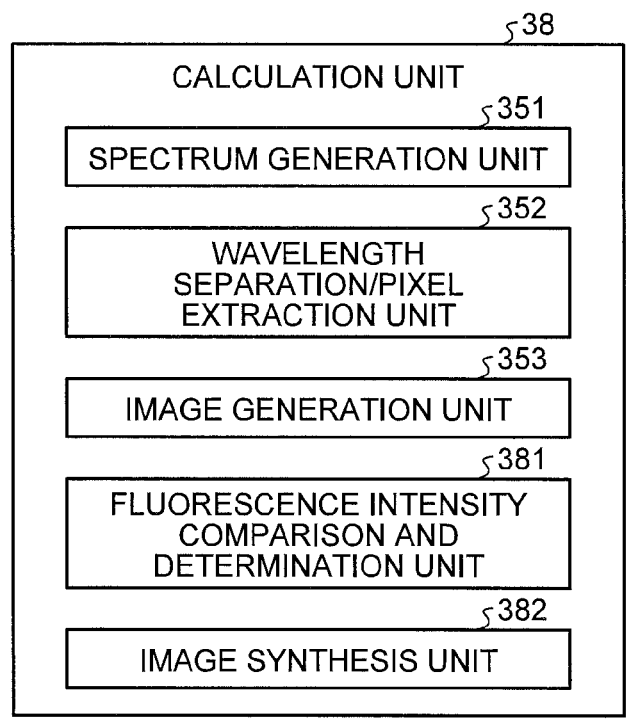
FIG. 11 is a block diagram illustrating a structure of a calculation unit according to a third embodiment of the present invention.

Next, a third embodiment of the present invention is described. FIG. 11 is a block diagram illustrating a structure of a calculation unit included in a microscope system according to the third embodiment. As illustrated in FIG. 11, the microscope system according to the third embodiment includes a calculation unit 38 that includes a fluorescence intensity comparison and determination unit 381 and an image synthesis unit 382 in addition to the structure of the calculation unit 35 illustrated in FIG. 1. The structure of the calculation unit 38 other than the fluorescence intensity comparison and determination unit 381 and the image synthesis unit 382, and the structure of the entire microscope system in the third embodiment are similar to those of the first embodiment.

The fluorescence intensity comparison and determination unit 381 selects, based on the fluorescence intensity, the pixel to be overlapped on the bright-field observation image of the specimen S stained for the bright-field observation from among the pixel group corresponding to the particular specimen component extracted from the fluorescence observation image. The image synthesis unit 382 generates the synthesis image by overlapping the particular specimen component on the bright-field observation image of the specimen S.

Figure 12:
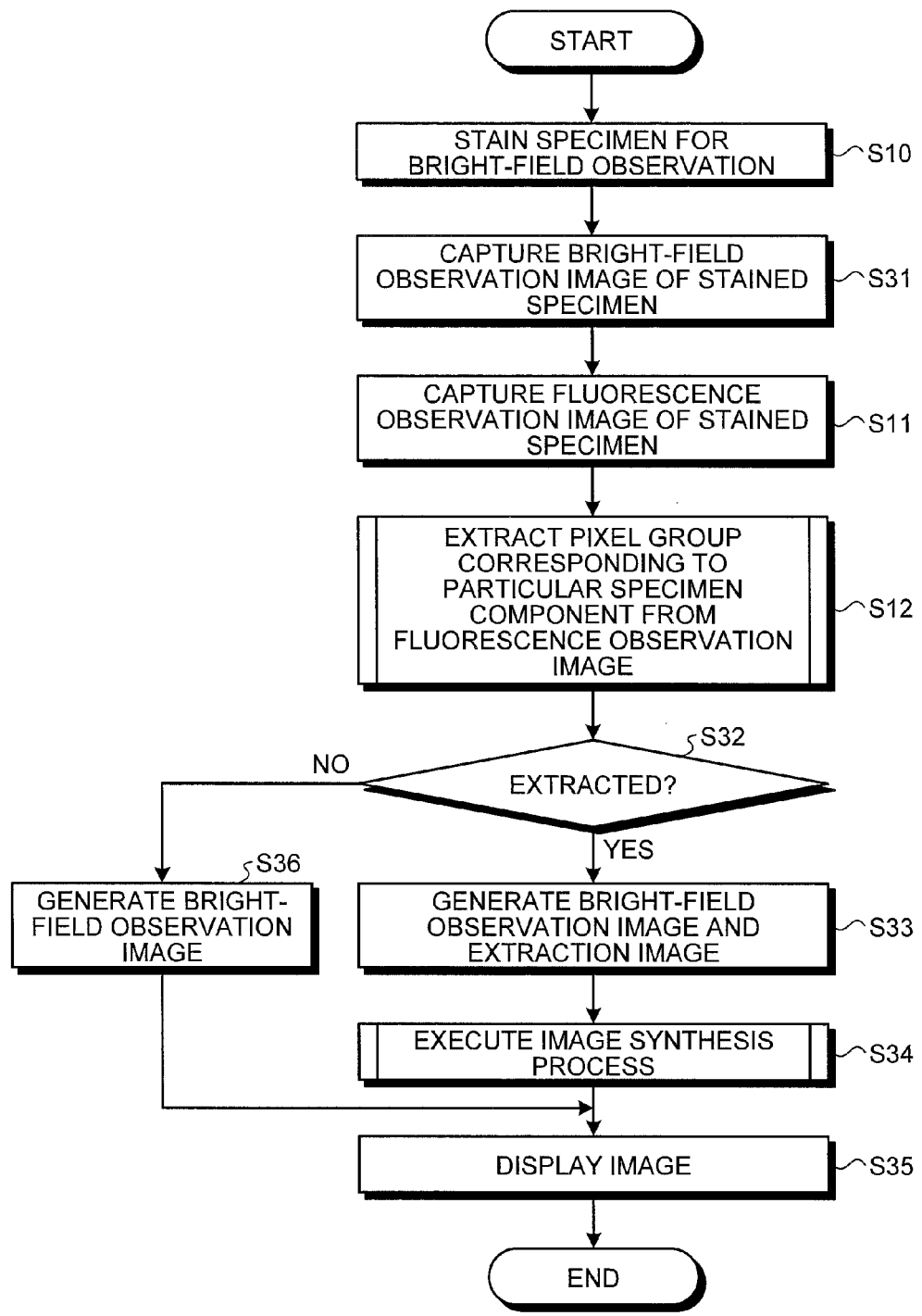
FIG. 12 is a flowchart illustrating a specimen observation method according to the third embodiment of the present invention.

Next, an image processing method according to the third embodiment is described. FIG. 12 is a flowchart illustrating a specimen observation method including the image processing method according to the third embodiment. In FIG. 12, the process in Steps S10, S11, and S12 is common to that of the first embodiment.

In Step S31 subsequent to Step S10, in the microscope system 1, the specimen S stained for the bright-field observation (for example, with the HE stain) is placed on the specimen stage 14 and the specimen S is irradiated from the transmission illumination light source 13 and the transmission illumination optical system 13a; thus, the bright-field observation image of the specimen S is captured. Note that, on this occasion, the optical cube 161 is absent in the observation optical path L$_O$ of the microscope device 10. The image data created in the imaging unit 20 are input to the image processing apparatus 30 through the image acquisition unit 32 and stored in the storage unit 34.

In Step S32 subsequent to Step S12, the calculation unit 38 determines whether the pixel group corresponding to the particular specimen component has been extracted or not. If the pixel group has been extracted (Yes in Step S32), the image generation unit 353 generates a bright-field observation image by reading from the storage unit 34 the image data generated by the capture in Step S31 and generates the extraction image on the basis of the extracted pixel group (Step S33). In the case where the plural pixel groups are extracted, the image generation unit 353 may generate the image for each pixel group or may generate the image using all the extracted pixel groups.

Figure 13:
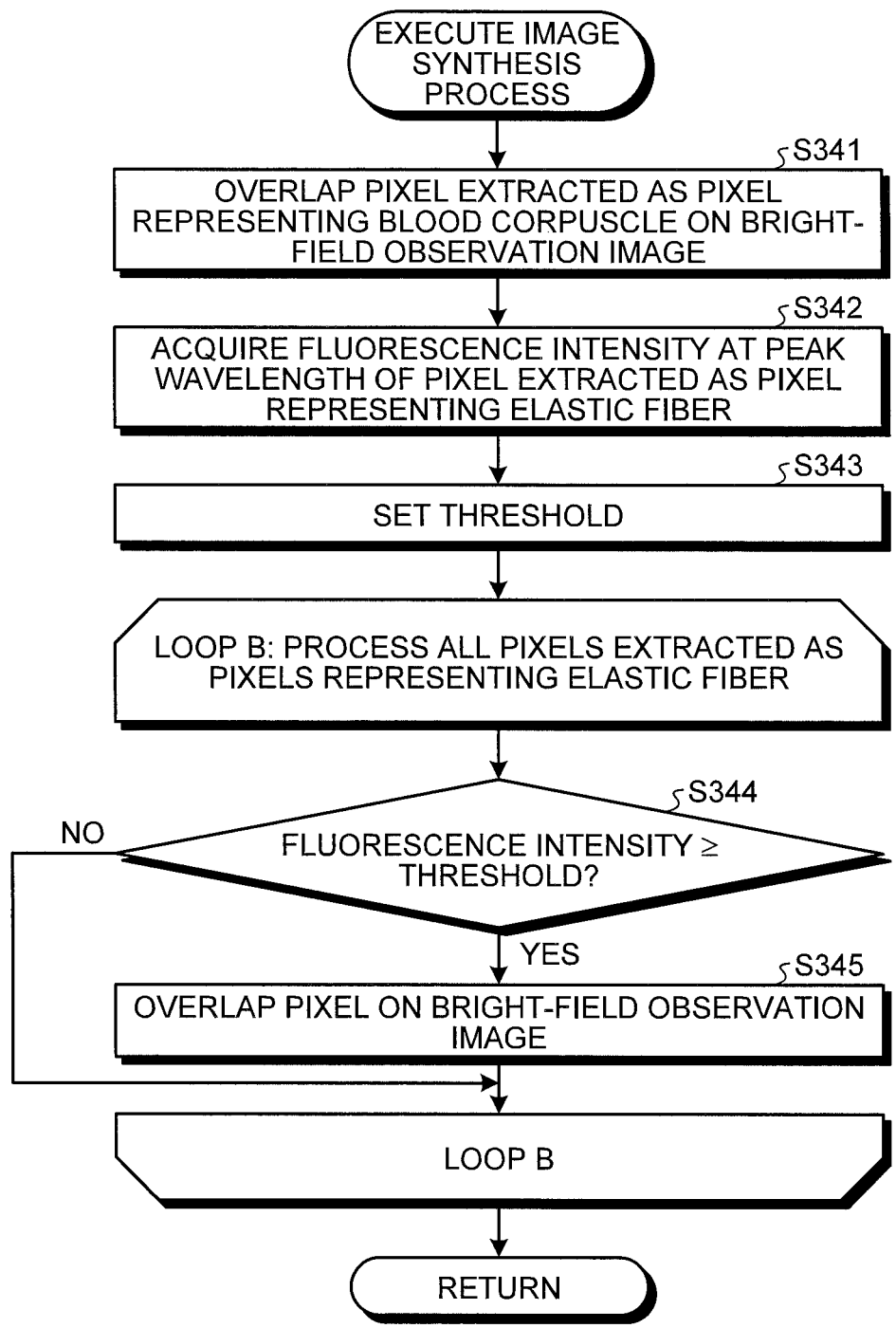
FIG. 13 is a flowchart illustrating the image synthesis process.

In the subsequent Step S34, the image synthesis unit 382 executes the image synthesis process for generating the synthesis image where the particular specimen component is overlapped on the bright-field observation image. FIG. 13 is a flowchart illustrating the detail of the image synthesis process in Step S34. In Step S34, the pixel group extracted in Step S12 may be simply overlapped on the bright-field observation image but in order to reduce the influence from the noise or the like in the extracted pixel group, the process as described below is preferably executed. Description is made of an example in which the pixel groups representing the blood corpuscle and the elastic fiber are extracted with reference to the fluorescence intensity spectra in FIG. 6 in Step S12.

First, in Step S341, the image synthesis unit 382 overlaps the pixel extracted as the one representing the blood corpuscle from the fluorescence observation image (see Step S124) on the bright-field observation image.

In the subsequent Step S342, the fluorescence intensity comparison and determination unit 381 acquires the fluorescence intensity (pixel value) at the peak wavelength (560 nm) of the pixel (see Step S127) extracted as the one representing the elastic fiber from the fluorescence observation image in Step S12.

In the subsequent Step S343, the fluorescence intensity comparison and determination unit 381 sets the threshold a. As the threshold a, for example, a value of 70% of the maximum value of the fluorescence intensity acquired in Step S342 is set.

Next, the calculation unit 38 executes the process of a loop B for all the pixels extracted as the ones representing the elastic fiber. In Step S344, the fluorescence intensity comparison and determination unit 381 determines whether the fluorescence intensity of the pixel to be processed is greater than or equal to the threshold a. If the fluorescence intensity is greater than or equal to the threshold a (Yes in Step S344), the image synthesis unit 382 overlaps the pixel to be processed on the bright-field observation image (Step S345). On the other hand, if the fluorescence intensity is less than the threshold a (No in Step S344), the operation of the calculation unit 38 transits to the process for the pixel to be processed next.

Here, the peak wavelength band in the fluorescence intensity spectrum of the elastic fiber is similar to the peak wavelength band of the noise or another specimen component (for example, cytoplasm), but not similar to that of the blood corpuscle. Therefore, the threshold is set in the third embodiment and only the pixel whose fluorescence intensity is remarkably high in the peak wavelength band is extracted as the elastic fiber, thereby eliminating the influence of the other specimen component or the noise.

When the process of the loop B has finished with respect to all the pixels extracted as the ones representing the elastic fiber, the process returns to the main routine.

In Step S35 subsequent to Step S34, the control unit 36 displays at least one of the synthesis image, the extraction image, and the bright-field observation image generated by the image generation unit 353 on the image display unit 33. In this case, the number of images and the positions thereof to be displayed on one screen are not particularly limited. For example, all of the bright-field observation image, the extraction image, and the synthesis image may be displayed on one screen, or just the synthesis image may be displayed on one screen. Alternatively, the synthesis image and the extraction image where the specimen component selected by a user is present may be displayed on one screen.

On the other hand, if the pixel group corresponding to the particular specimen component is not extracted in Step S32 (No in Step S32), the control unit 36 displays only the bright-field observation image on the image display unit 33 (Step S36).

As thus described, since the synthesis image is generated in which the particular specimen component is overlapped on the bright-field observation image in the third embodiment, the user can observe the entire image of the specimen S and the particular specimen component while comparing the both correctly.

Third Modified Example

A third modified example of the first to third embodiments of the present invention is described. The first to third embodiments have described the case in which the plural specimen components that generate the autofluorescence with different wavelengths are present in the fluorescence observation image. However, the wavelengths of the autofluorescence emitted from the plural specimen components may coincide with each other depending on the kind of the pigment for the bright-field observation that stains the specimen S, the specimen components, or the combination thereof.

Figure 14:
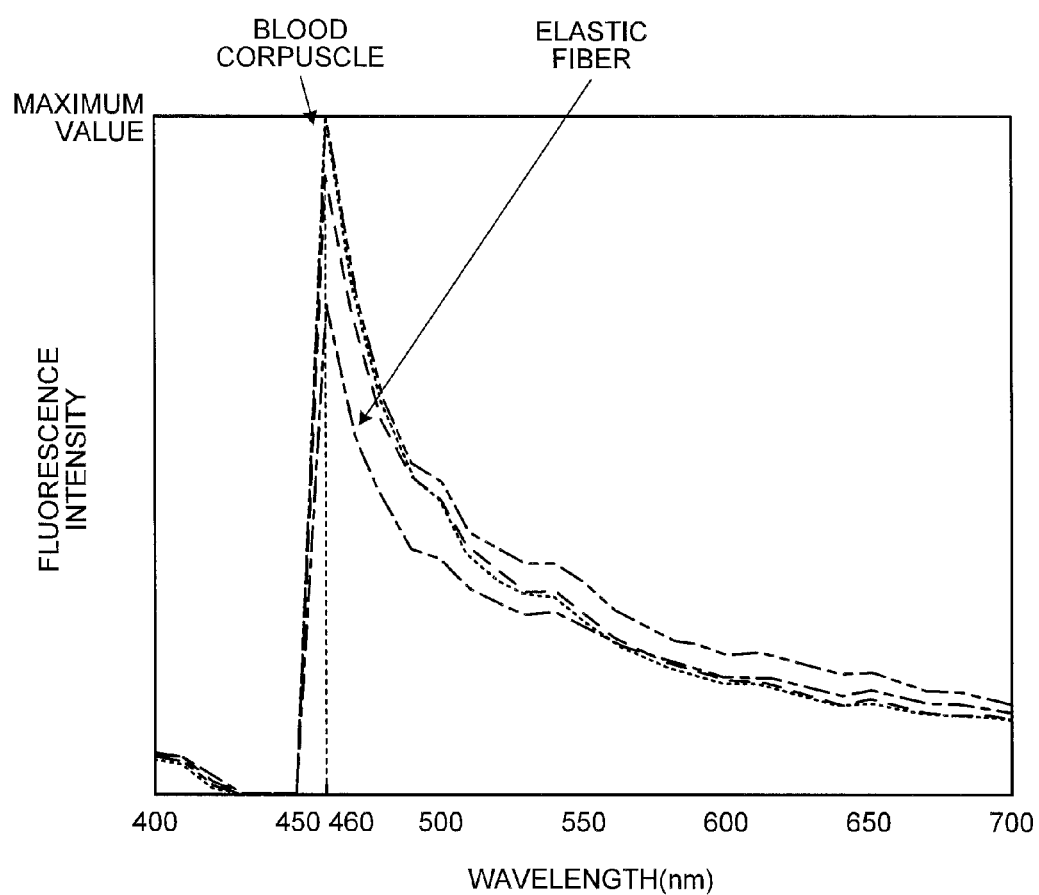
FIG. 14 is a graph representing a part of the fluorescence intensity spectrum in the fluorescence observation image of the specimen stained with eosin only.

For example, it has been clarified by the experiments of the present inventor that when the specimen stained with hematoxylin only is irradiated with the excitation light with a wavelength band ranging from about 300 nm to 400 nm, the autofluorescence with a wavelength of around 460 nm is produced from the elastic fiber and the blood corpuscle as illustrated in FIG. 14.

In the process (see Step S121 of FIG. 5) of acquiring the fluorescence intensity spectrum of each pixel in the fluorescence observation image of this specimen, one wavelength with the highest peak intensity is selected and the pixel group whose fluorescence intensity becomes the peak at that wavelength is extracted. Thus, the pixel groups representing the specimen components (elastic fiber and blood corpuscle) that generate the autofluorescence can be extracted collectively.

For the specimen as above, the wavelength with the highest peak intensity is selected and the pixel group whose fluorescence intensity becomes the peak at the wavelength is extracted, and in addition to that, the pixels are classified according to the fluorescence intensity at that wavelength, whereby the extracted pixel groups can be separated for each specimen component. For example, in the case of FIG. 14, the threshold is set to approximately 75% of the maximum value of the fluorescence intensity at the selected wavelength, and based on the threshold, the extracted pixel groups may be classified. Thus, the pixel group representing the blood corpuscle (pixel group whose peak intensity is higher than the threshold) and the pixel group representing the elastic fiber (pixel group whose peak intensity is lower than the threshold) can be extracted separately.

Figure 15:
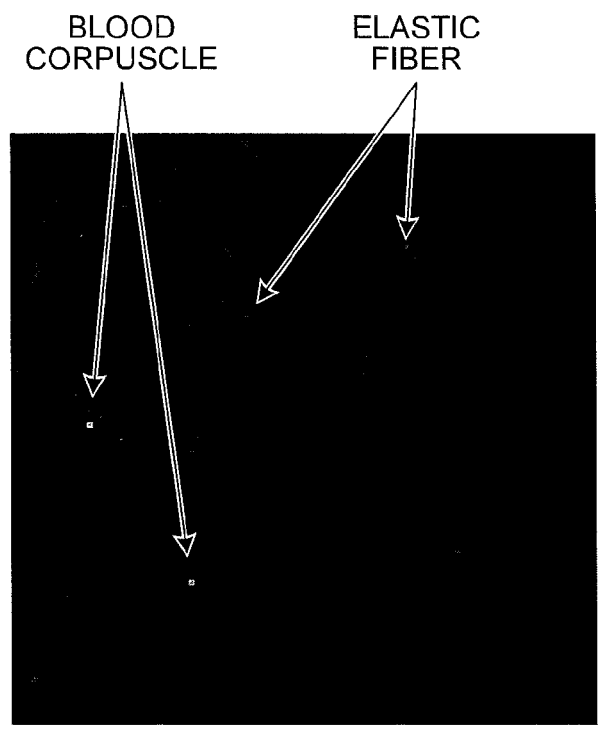
FIG. 15 is an example of displaying the extraction image representing the elastic fiber and the blood corpuscle extracted from the fluorescence observation image based on the fluorescence intensity spectrum illustrated in FIG. 14.

FIG. 15 is an example of displaying the extraction images representing the elastic fiber and the blood corpuscle extracted from the fluorescence observation image based on the fluorescence intensity spectrum illustrated in FIG. 14. In this case, since the extracted specimen components have the similar color, a different color is preferably allocated to the pixel representing any one of the specimen components when the extracted image is displayed.

As thus described, in the case where the plural kinds, of specimen components in the fluorescence observation image generate the autofluorescence with the wavelength of the same degree, the pixel groups are classified based on the fluorescence intensity; thus, the specimen components can be separated correctly for each kind.

Fourth Modified Example

Figure 16:
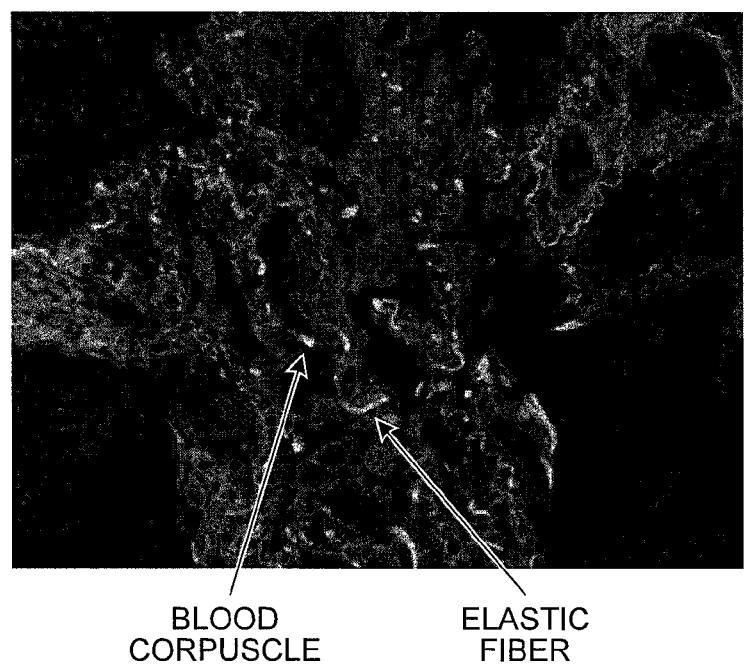
FIG. 16 is another example of displaying the fluorescence observation image of the same specimen as that in FIG. 3.
Figure 17:
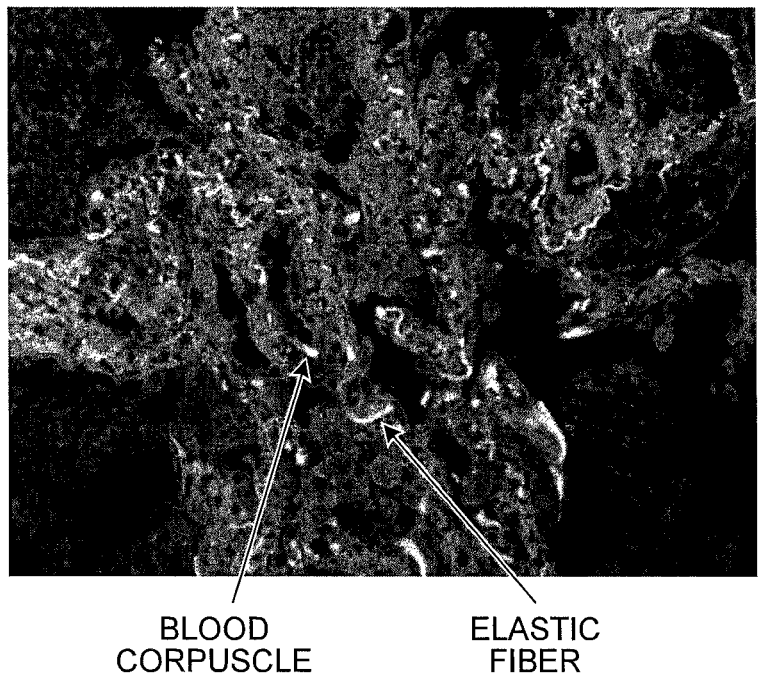
FIG. 17 is still another example of displaying the fluorescence observation image of the same specimen as that in FIG. 3.

A fourth modified example of the first to third embodiments of the present invention is described. When the fluorescence observation image of the specimen stained for the bright-field observation is captured, the fluorescence cube U-MWU is used in the first to third embodiments; however, other fluorescence cubes such as the fluorescence cube U-MWIBA or U-MWIG manufactured by OLYMPUS Corp. can also be used. FIG. 16 is the fluorescence observation image of the specimen corresponding to the image M1 of FIG. 3, which is captured using the same fluorescence cube U-MWIBA and seems greenish as a whole. FIG. 17 is the fluorescence observation image of the specimen corresponding to the image M1, which is captured using the same fluorescence cube U-MWIG and seems orange as a whole.

As illustrated FIG. 16 and FIG. 17, the entire fluorescence observation image has the similar color in the case of using these fluorescence cubes; therefore, the peak wavelength in the fluorescence intensity spectrum in the elastic fiber region and the peak wavelength in the fluorescence intensity spectrum in the blood corpuscle region are close to each other. In this case, in a manner similar to the third modified example, after the pixel representing the elastic fiber and the pixel representing the blood corpuscle are extracted based on the peak wavelength of the fluorescence intensity spectrum, the pixel representing the elastic fiber and the pixel representing the blood corpuscle may be separated from each other on the basis of the fluorescence intensity.

Fifth Modified Example

A fifth modified example of the first to third embodiments of the present invention is described next. In the first to third embodiments, the HE stain known as the dye for the morphological observation is used for staining the specimen; however, any dye may be used as long as the bright-field observation is possible.

Figure 18:
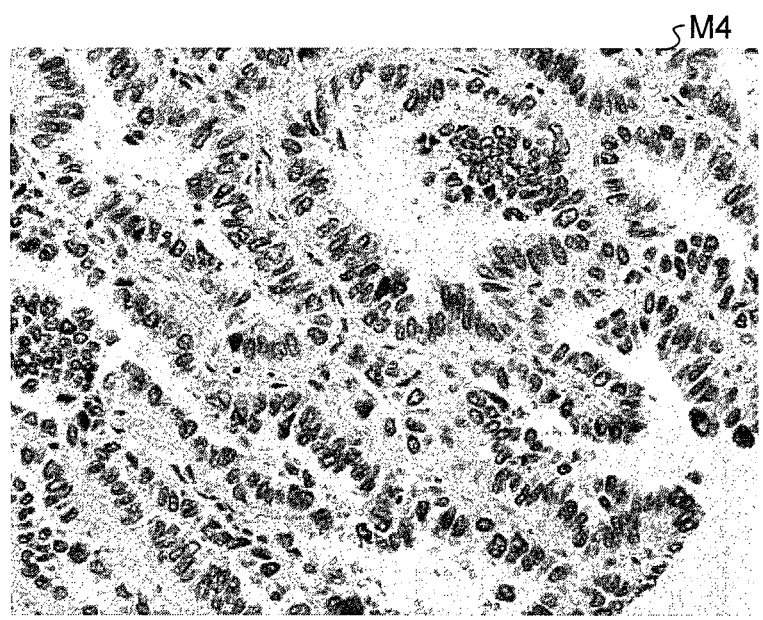
FIG. 18 is an example of displaying the bright-field observation image of the specimen stained with the HDABNF.
Figure 19:
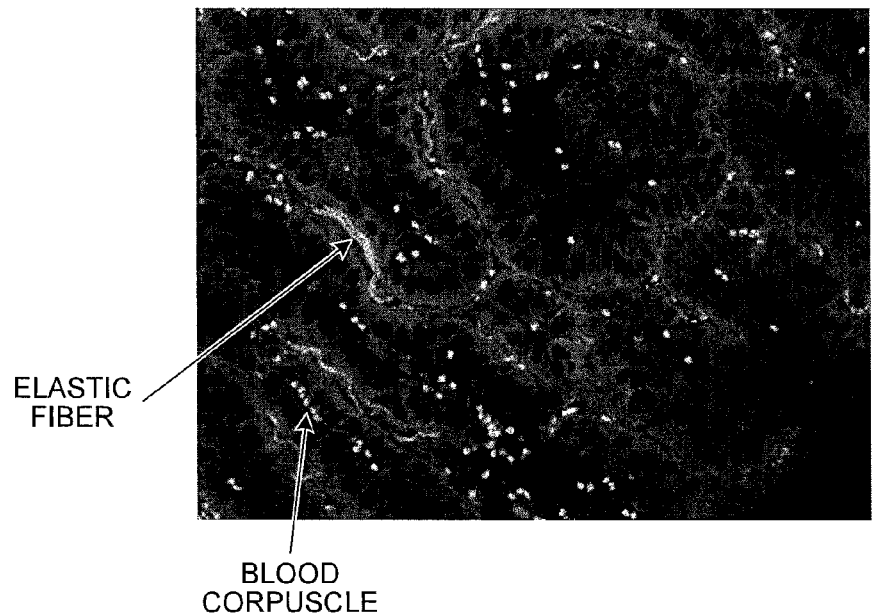
FIG. 19 is an example of displaying the fluorescence observation image of the same specimen as that in FIG. 18.

For example, FIG. 18 is an example of displaying the bright-field observation image of the specimen stained with the HDABNF (H: hematoxylin, DAB: diaminobenzidine, NF: New Fuchsin) for the bright-field observation. When the fluorescence observation is conducted relative to the same specimen as the bright-field observation image M4 with the use of the fluorescence cube U-MWU, the fluorescence observation image as illustrated in FIG. 19 can be acquired. In this fluorescence observation image, the elastic fiber region and the blood corpuscle region that are stained with hematoxylin are displayed in bluish color. Moreover, the region stained with DAB is displayed blackish as compared to the background region or the region stained with hematoxylin. Moreover, the region stained with NF is displayed in reddish color.

In this case, the peak wavelength in the fluorescence intensity spectrum in the elastic fiber region and the peak wavelength in the fluorescence intensity spectrum in the blood corpuscle region are close to each other. In this case, in a manner similar to the third modified example, after the pixel representing the elastic fiber and the pixel representing the blood corpuscle are extracted based on the peak wavelength of the fluorescence intensity spectrum, the pixel representing the elastic fiber and the pixel representing the blood corpuscle may be separated from each other based on each fluorescence intensity.

Figure 20:
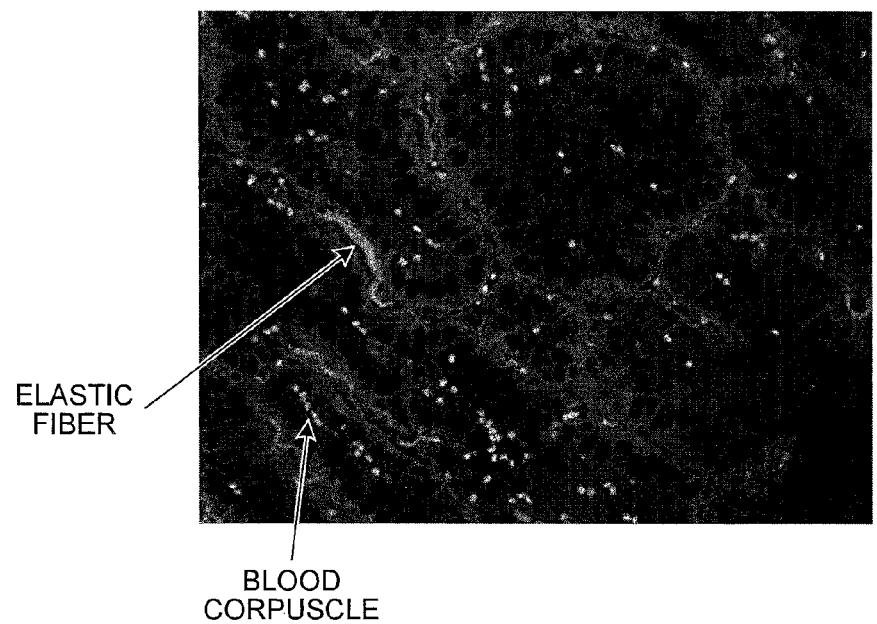
FIG. 20 is another example of displaying the fluorescence observation image of the same specimen as that in FIG. 18.

For example, as a result of the fluorescence observation of the same specimen as the bright-field observation image M4 illustrated in FIG. 18 through the fluorescence cube U-MWIBA, the fluorescence observation image as illustrated in FIG. 20 can be acquired. In this fluorescence observation image, the elastic fiber region and the blood corpuscle region that are stained with hematoxylin are both displayed in yellow-greenish color. Note that the region stained with DAB is displayed blackish as compared to the background region or the region stained with hematoxylin. Note that the region stained with NF cannot be distinguished on the fluorescence observation image as illustrated in FIG. 20.

Even in this case, the peak wavelength in the fluorescence intensity spectrum in the elastic fiber region and the peak wavelength in the fluorescence intensity spectrum in the blood corpuscle region are close to each other; therefore, the pixel representing the elastic fiber and the pixel representing the blood corpuscle can be separately extracted in a manner similar to the third modified example.

Figure 21:
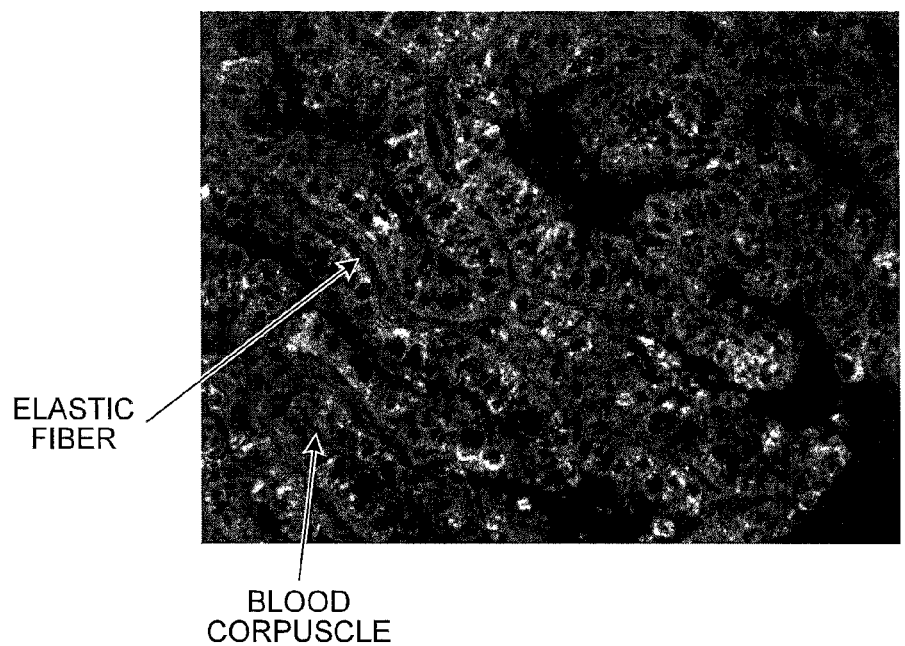
FIG. 21 is still another example of displaying the fluorescence observation image of the same specimen as that in FIG. 18.

For example, as a result of the fluorescence observation of the same specimen as the bright-field observation image M4 illustrated in FIG. 18 through the fluorescence cube U-MWIG, the fluorescence observation image as illustrated in FIG. 21 can be acquired. In this fluorescence observation image, the elastic fiber region and the blood corpuscle region that are stained with hematoxylin are both displayed in reddish color. The nucleus that is stained with hematoxylin but does not produce the autofluorescence is displayed in grayish color. The region stained with DAB is displayed blackish as compared to the background region or the region stained with hematoxylin. Moreover, the portion stained with NF has the highest fluorescence intensity.

In this case, when the pixels representing the elastic fiber and the blood corpuscle are extracted, first, the wavelength at which the peak intensity of the fluorescence intensity is the second highest is selected. Then, after the pixel whose fluorescence intensity is the peak at that wavelength is extracted, the pixel representing the elastic fiber and the pixel representing the blood corpuscle may be separated based on the fluorescence intensity.

In addition, the dye that is applicable in the first to third embodiments includes the hematoxylin-DAB stain, the hematoxylin-New Fuchsin stain, and the hematoxylin simple stain. Here, if the pigment that stains the specimen includes hematoxylin, the bright-field observation image of the specimen displays the cell nucleus. Therefore, in the case of using the specimen that has been stained with the above dye, the cell nucleus displayed in the bright-field observation image and the elastic fiber and the blood corpuscle extracted from the fluorescence observation image can be observed while comparing the all. In this case, the fluorescence cube that selects the fluorescence light around 450 nm to 550 nm is preferably used. This can separate the peak wavelength the most clearly in the spectra of the autofluorescence generated from the elastic fiber and the blood corpuscle. Therefore, the pixel representing the elastic fiber and the pixel representing the blood corpuscle can be separately extracted accurately.

Fourth Embodiment

Next, a fourth embodiment of the present invention is described. The above first to third embodiments have described the image processing for extracting and displaying the elastic fiber and the blood corpuscle as the specimen components from the fluorescence observation image; on the other hand, the fourth embodiment will describe the automatic diagnosis of the pathological change based on the extracted elastic fiber.

Here, JP 2003-506016 W discloses a method of diagnosing the arterial wall disruptive disorders. The diagnosis disclosed in JP 2003-506016 W requires the genetic test or the test by the antibody coupled with the marker, which requires the cost for the reagent and labor. In view of this, the technique for facilitating the diagnosis on the abnormality related to the blood vessel such as the arterial wall disruptive disorders without requiring the cost for the reagent has been anticipated. However, it has been very difficult to determine the thickness or the continuity of the artery or vein, which is the indicator of the abnormality related to the blood vessel, on the basis of the specimen that is not stained with the specific dye (unstained specimen or HE-stained specimen).

In view of this, in the fourth embodiment, description is made of an image processing apparatus, a microscope system, and an image processing method, which can automatically determine the abnormality in the blood vessel of the specimen, specifically the vascular invasion, on the basis of the image obtained by capturing the specimen that is not stained with the specific dye.

Figure 22:
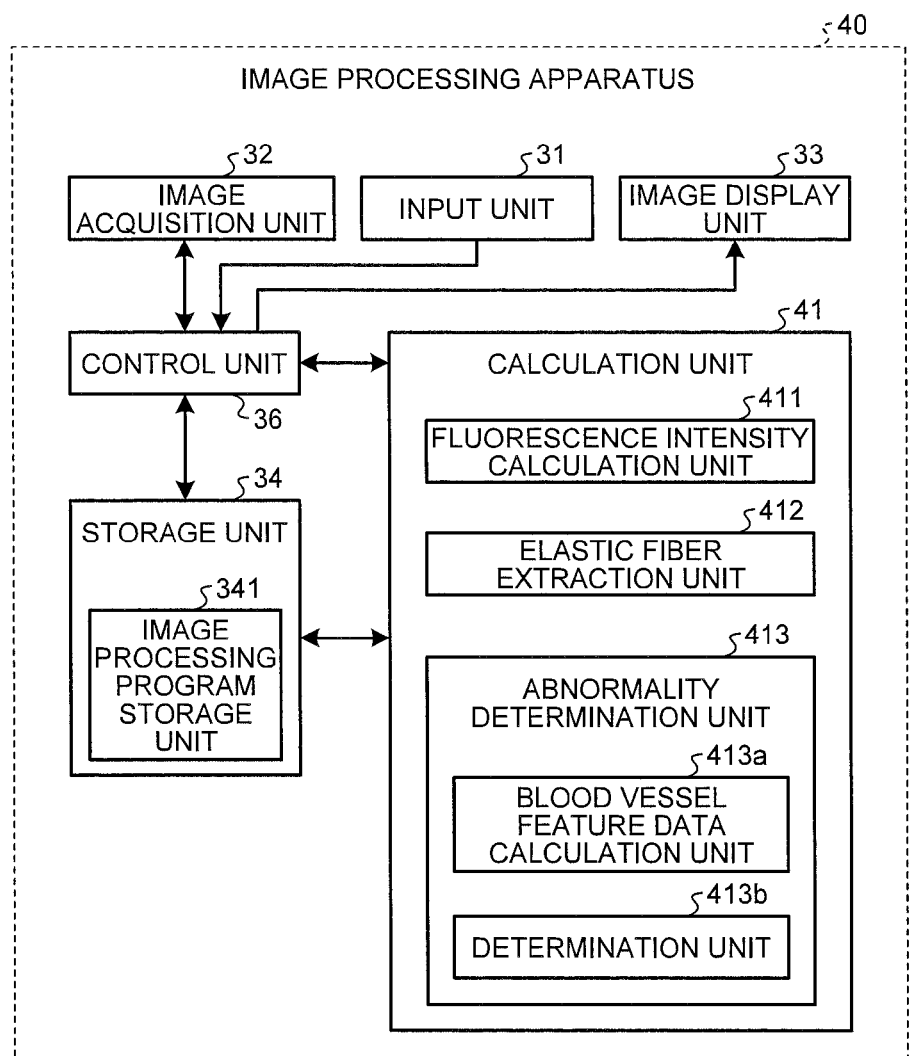
FIG. 22 is a block diagram illustrating a structure of an image processing apparatus according to a fourth embodiment of the present invention.

FIG. 22 is a block diagram illustrating a structure of the image processing apparatus according to the fourth embodiment. The microscope system according to the fourth embodiment includes an image processing apparatus 40 illustrated in FIG. 22 instead of the image processing apparatus 30 illustrated in FIG. 1. The structure and the operation of the microscope device 10 and the imaging unit 20 are similar to those of the first embodiment.

The image processing apparatus 40 includes the input unit 31, the image acquisition unit 32, the image display unit 33, the storage unit 34, the control unit 36, and a calculation unit 41. Among those units, the structure and the operation of the units other than the calculation unit 41 are similar to those of the first embodiment. In the fourth embodiment, the image processing program storage unit 341 stores an image processing program for determining the presence or absence of the vascular invasion on the basis of the fluorescence intensity in the fluorescence observation image.

The calculation unit 41 includes, for example, a hardware device such as a CPU, and reads in the image processing program stored in the image processing program storage unit 341 stored in the storage unit 34, thereby executing the image processing for determining the presence or absence of the vascular invasion on the basis of the image data acquired by the image acquisition unit 32 and stored in the storage unit 34 and the fluorescence intensity of the fluorescence observation image of the specimen S that is not stained or is stained for the bright-field observation with, for example, the HE stain.

The calculation unit 41 includes: a fluorescence intensity calculation unit 411 for calculating as the fluorescence intensity, the value corresponding to the intensity of the fluorescence emitted from the specimen that has been irradiated with the excitation light on the basis of the image information (image data) of the fluorescence observation image; an elastic fiber extraction unit 412 for extracting the elastic fiber on the basis of the fluorescence intensity calculated by the fluorescence intensity calculation unit 411; and an abnormality determination unit 413 for determining the presence or absence of the abnormality in the blood vessel in the fluorescence observation image on the basis of the state of the extracted elastic fiber.

In the fourth embodiment, the abnormality determination unit 413 includes a blood vessel feature data calculation unit 413a for calculating the morphological feature data of the blood vessel including the elastic fiber from the extracted elastic fiber, and a determination unit 413b for determining the presence or absence of the abnormality in the blood vessel on the basis of the morphological feature data of the blood vessel.

Here, the morphological feature data of the blood vessel is obtained by quantifying the morphological features such as the size or shape of the blood vessel. In the fourth embodiment, the circularity of the sectional shape of the blood vessel is used as the morphological feature data. The shape becomes more circular as the value of circularity is closer to 1. In the case of the normal blood vessel, the sectional shape is more circular and the value of circularity is closer to 1. On the contrary, in the case of the abnormal blood vessel, the sectional shape is flat and the value of circularity is deviated from 1.

Figure 23:
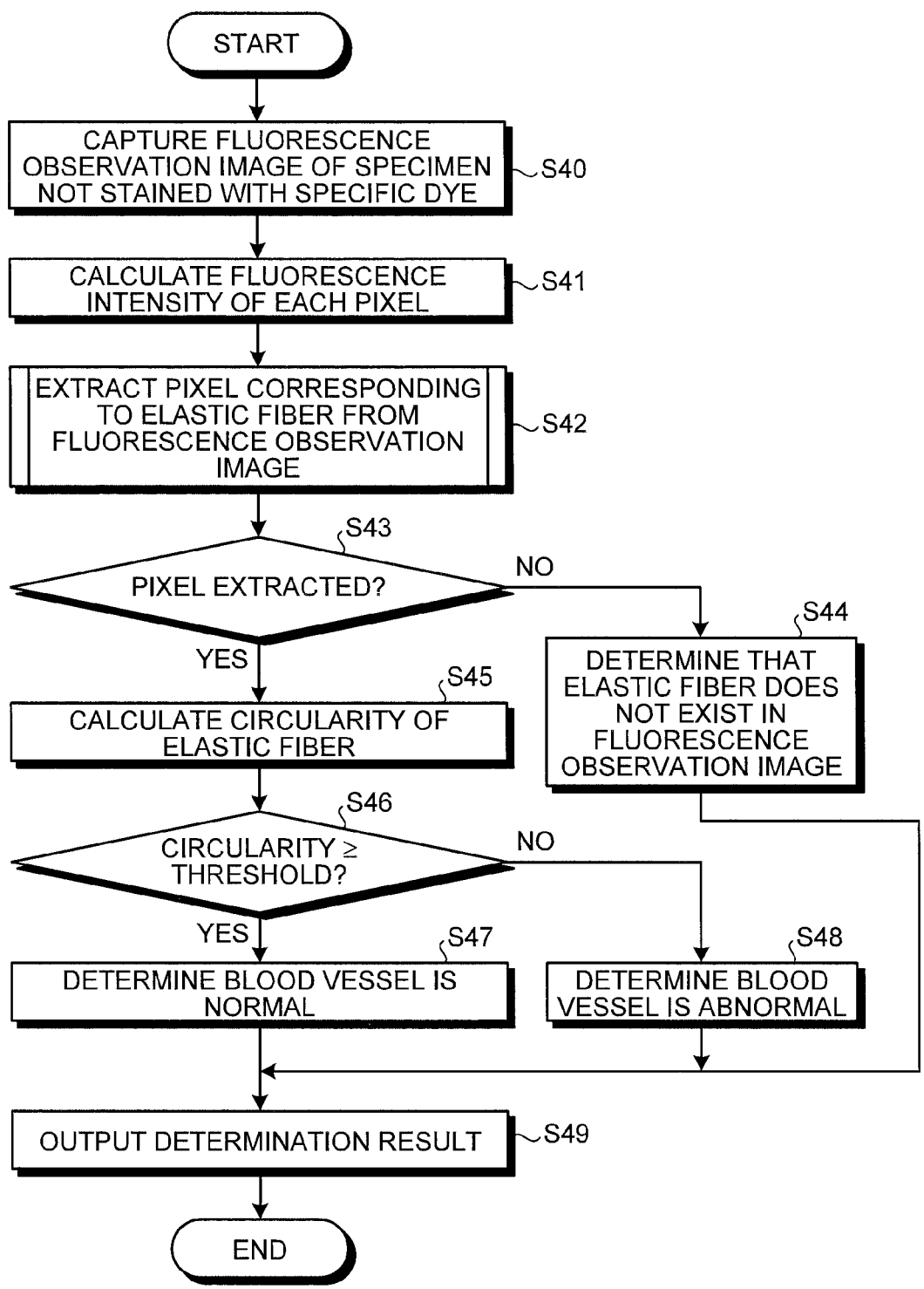
FIG. 23 is a flowchart illustrating a specimen observation method according to the fourth embodiment.

Next, the image processing method according to the fourth embodiment is described. FIG. 23 is a flowchart illustrating a specimen observation method including the image processing method according to the fourth embodiment. First, in Step S40, the fluorescence observation image of the specimen that is not stained with the specific dye is captured. In other words, the pathological specimen (specimen S) that is not stained or is stained with HE is placed on the specimen stage 14 (see FIG. 1), and is irradiated with the excitation light from the epi-illumination light source 12 and the epi-illumination optical system 12a, and the image is captured in a plurality of bands with the imaging unit 20. Thus, the image data of the observation image represented by the fluorescence light generated from the specimen S is input to the image processing apparatus 40 through the image acquisition unit 32, and then stored in the storage unit 34. The details of the imaging operation are similar to those of Step S11 in the first embodiment.

Figure 24A:
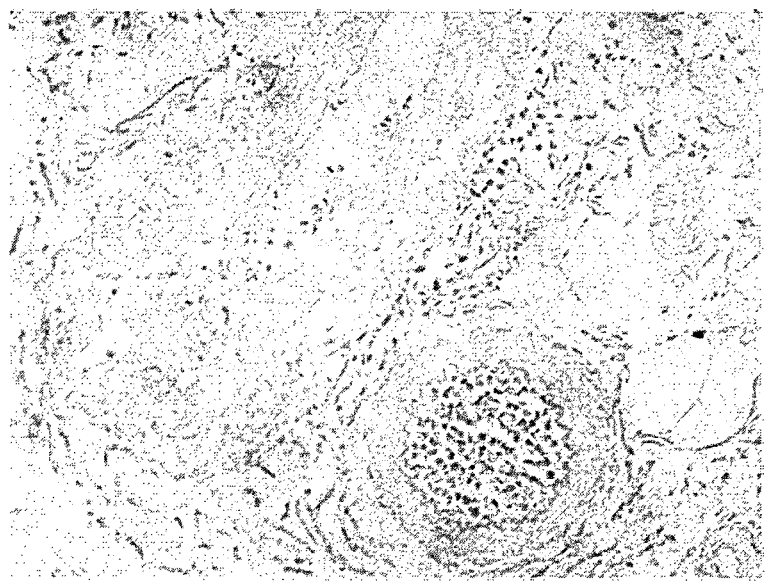
FIG. 24A is the bright-field observation image of the unstained specimen of the normal human colon.
Figure 24B:
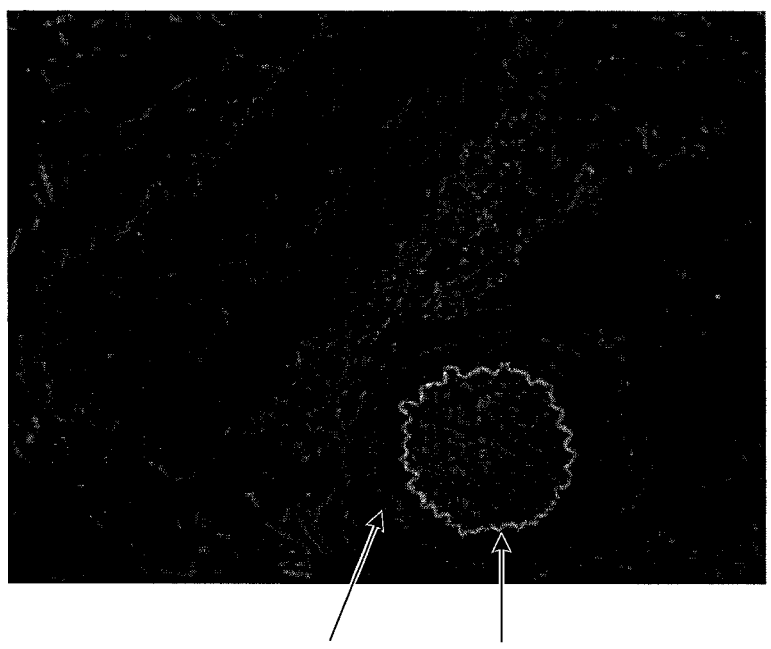
FIG. 24B is the fluorescence observation image of the same unstained specimen as that in FIG. 24A.

FIG. 24A is the bright-field observation image of the unstained specimen of the normal human colon, and FIG. 24B is the fluorescence observation image of the same unstained specimen. These images are obtained by capturing the prepared specimen that is formed by embedding the pathological specimen in paraffin, slicing the paraffin with a microtome, fixing the paraffin on a slide, and adhering the cover glass with a sealant. The fluorescence observation image is obtained by the irradiation with the excitation light having a wavelength of 300 nm to 400 nm and the capture with a CCD camera having an imaging wavelength of 400 nm to 700 nm.

Figure 25A:
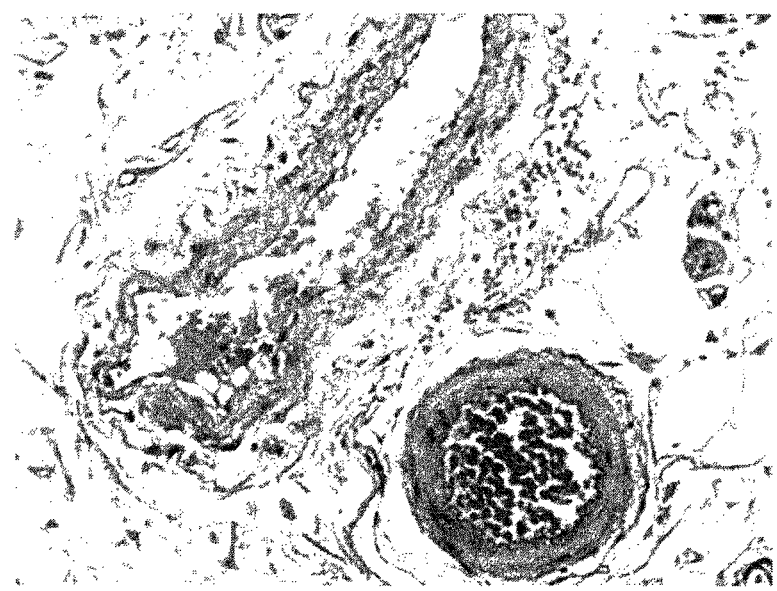
FIG. 25A is the bright-field observation image of the HE-stained specimen of the normal human colon.
Figure 25B:
FIG. 25B is the fluorescence observation image of the same HE-stained specimen as that in FIG. 25A.

FIG. 25A is the bright-field observation image of the HE-stained specimen that is the same pathological specimen as that of FIG. 24A, and FIG. 25B is the fluorescence observation image of the same HE-stained specimen. These images are obtained by capturing the prepared specimen that is formed by fixing the sliced specimen of the pathological specimen on the slide and then staining the specimen with the HE. The excitation light and the imaging wavelength for the fluorescence observation image are similar to those of FIG. 24B.

As illustrated in FIG. 24A, the specimen components are hardly observable in the bright-field observation image of the unstained specimen. In contrast to this, the elastic fiber that emits the autofluorescence is extracted in the fluorescence observation image illustrated in FIG. 24B.

Moreover, as illustrated in FIG. 25A, various specimen components are displayed in the bright-field observation image of the HE-stained specimen; however, the elastic fiber is hardly observed. On the other hand, in the fluorescence observation image illustrated in FIG. 25B, the elastic fiber and the blood corpuscle that emit the autofluorescence among the specimen components are extracted.

In the subsequent Step S41, the calculation unit 41 reads out the image data of the fluorescence observation image captured in Step S40 from the storage unit 34, and calculates the fluorescence intensity of each pixel by the fluorescence intensity calculation unit 411. The fluorescence intensity of each pixel is given by, for example, the pixel value or the luminance value calculated from the pixel value.

Figure 26:
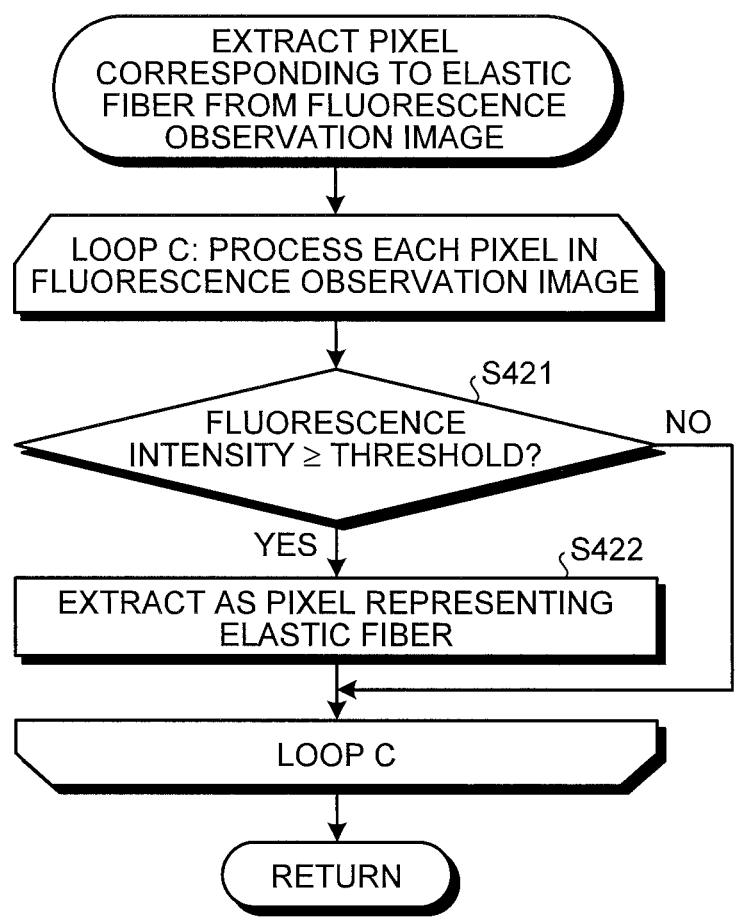
FIG. 26 is a flowchart illustrating the process to be executed by the elastic fiber extraction unit illustrated in FIG. 22.

In the subsequent Step S42, the elastic fiber extraction unit 412 extracts the pixel corresponding to the elastic fiber from the fluorescence observation image. FIG. 26 is a flowchart illustrating the process to be executed by the elastic fiber extraction unit 412. The elastic fiber extraction unit 412 executes the process of a loop C for each pixel in the fluorescence observation image.

In Step S421, the elastic fiber extraction unit 412 determines whether the fluorescence intensity of the pixel to be processed is greater than or equal to a specified threshold.

If the fluorescence intensity is greater than or equal to the threshold (Yes in Step S421), the elastic fiber extraction unit 412 extracts the pixel as the pixel representing the elastic fiber (Step S422). On the other hand, if the fluorescence intensity is less than the threshold (No in Step S421), the elastic fiber extraction unit 412 does not extract the pixel and transits to the process for the next pixel.

Figure 27:
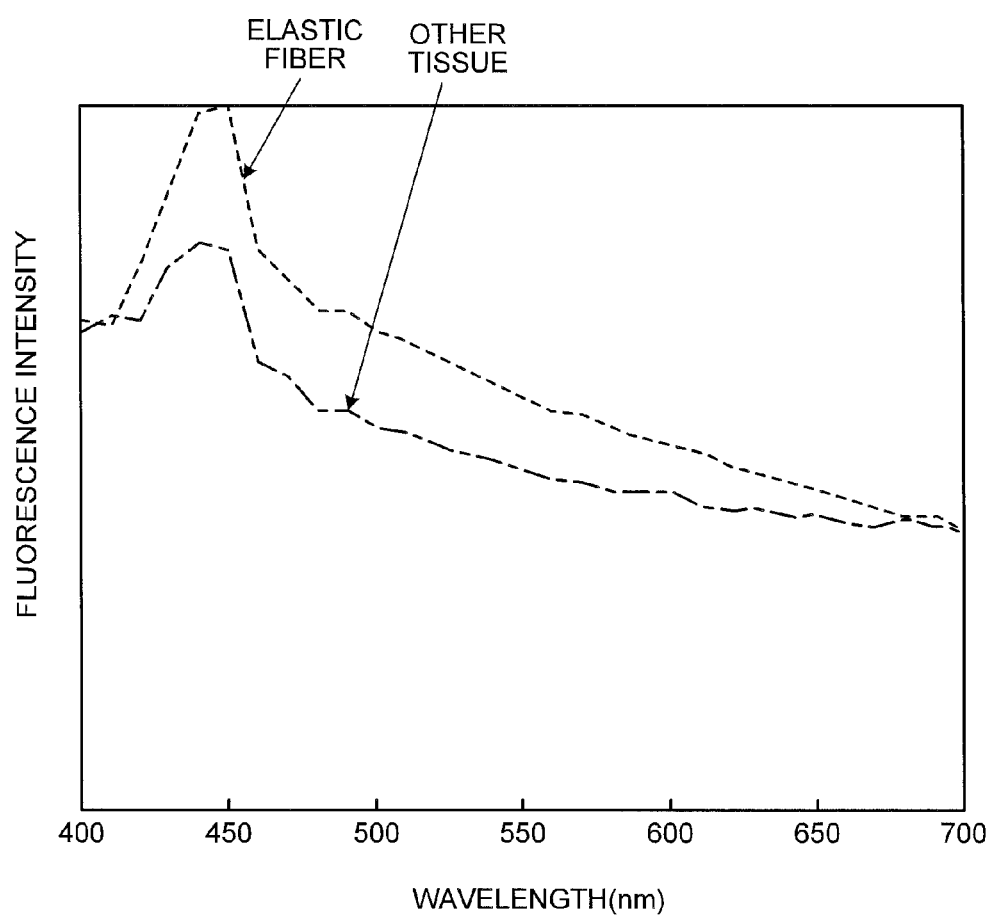
FIG. 27 is a graph of the fluorescence intensity spectrum in the fluorescence observation image of the unstained specimen illustrated in FIG. 24B.

Here, FIG. 27 is a graph of the fluorescence intensity spectrum in the fluorescence observation image of the unstained specimen illustrated in FIG. 24B. In the fluorescence observation image of the unstained specimen, the spectrum waveform representing the elastic fiber is observed at the remarkably high intensity relative to the spectrum waveform representing the other tissues as illustrated in FIG. 27. Therefore, in this case, the pixel representing the elastic fiber can be extracted based on the comparison between the fluorescence intensity of each pixel and the threshold.

On the other hand, in the fluorescence observation image of the HE-stained specimen, the spectrum waveform of the elastic fiber with a peak around 560 nm and the spectrum waveform of the blood corpuscle with a peak around 570 nm are observed as illustrated in FIG. 6. In this case, as a result of comparing the fluorescence intensity of each pixel and the threshold, the pixel representing the elastic fiber and the pixel representing the blood corpuscle may be extracted in a mixed state. However, since the blood corpuscle is generally smaller than the elastic fiber in size, the pixel representing the blood corpuscle is eliminated in the process of calculating the circularity to be described below, and as a result, the elastic fiber with a peak of a spectrum waveform around 560 nm can be extracted.

After the end of the process of the loop C for all the pixels in the fluorescence observation image, the operation of the calculation unit 41 returns to the main routine.

In Step S43 subsequent to Step S42, the abnormality determination unit 413 determines whether the pixel has been extracted by the elastic fiber extraction unit 412. If the pixel has not been extracted (No in Step S43), the abnormality determination unit 413 determines that the elastic fiber does not exist in the fluorescence observation image (Step S44) and thus ends the operation.

On the other hand, if the pixel has been extracted by the elastic fiber extraction unit 412 (Yes in Step S43), the blood vessel feature data calculation unit 413a calculates the circularity of the extracted pixel region (i.e., the elastic fiber) (Step S45). On this occasion, the lower limit of the area (number of pixels) of the pixel region for which the circularity is to be calculated is preferably set in advance. Thus, the pixel representing the blood corpuscle that has been extracted with the elastic fiber can be eliminated from the calculation target.

In the subsequent Step S46, the determination unit 413b determines whether the calculated circularity is greater than or equal to a specified threshold. If the circularity is greater than or equal to the threshold (Yes in Step S46), the determination unit 413b determines that the blood vessel including the elastic fiber is normal (Step S47). For example, in the case of the fluorescence observation image illustrated in FIG. 24B and FIG. 25B, since the shape of the extracted elastic fiber is close to a circular shape, the blood vessel is determined to be normal.

On the other hand, if the circularity is less than the threshold (No in Step S46), the determination unit 413b determines that the blood vessel including the elastic fiber is abnormal (Step S48).

In Step S49, the calculation unit 41 outputs the determination result made by the determination unit 413b and displays the result on the image display unit 33, and then stores the result in the storage unit 34. On this occasion, the fluorescence observation image from which the elastic fiber has been extracted may be displayed on the image display unit 33. After that, the calculation unit 41 ends the process for the fluorescence observation image.

As described above, according to the fourth embodiment, the presence or absence of the abnormality (vascular invasion) in the blood vessel in the specimen can be automatically determined using the fluorescence observation image of the specimen that is not stained or is stained with HE. In other words, in the fourth embodiment, the elastic fiber forming the blood vessel is extracted by detecting the autofluorescence generated from the specimen that is not stained or is stained with HE, and the feature data representing the state of the blood vessel are calculated based on the elastic fiber. Therefore, the presence or absence of the abnormality in the blood vessel can be estimated by the automatic process.

Thus, as compared to the case of analyzing the image of the specifically stained specimen, the equivalent or more pieces of diagnosis information can be acquired easily and at low cost according to the fourth embodiment, and the stable diagnosis support for the blood vessel can be conducted without the human labor.

Fifth Embodiment

Figure 28:
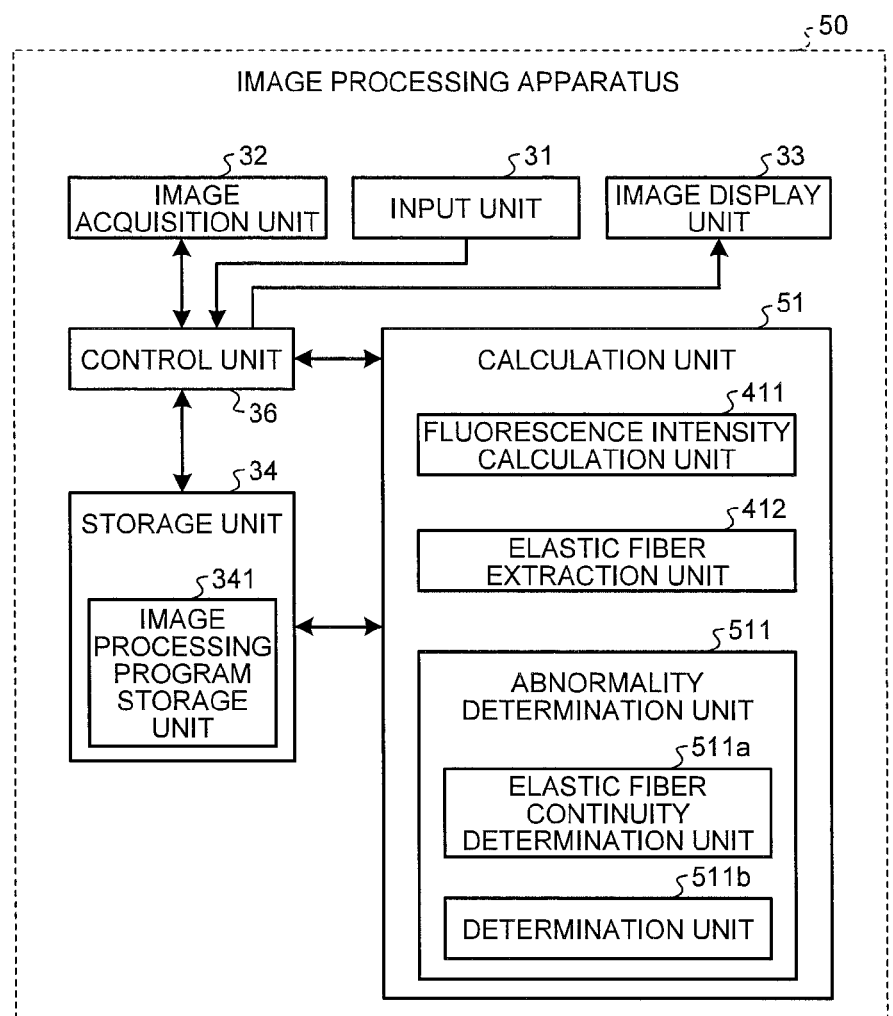
FIG. 28 is a block diagram illustrating a structure of an image processing apparatus according to a fifth embodiment of the present invention.

Next, a fifth embodiment of the present invention is described. FIG. 28 is a block diagram illustrating a structure of an image processing apparatus according to the fifth embodiment. A microscope system according to the fifth embodiment includes an image processing apparatus 50 having a calculation unit 51 instead of the image processing apparatus 30 illustrated in FIG. 1. Note that the structure and the operation of the microscope device 10 and the imaging unit 20 and the structure and the operation of the units of the image processing apparatus 50 other than the calculation unit 51 are similar to those of the fourth embodiment.

The calculation unit 51 includes an abnormality determination unit 511 instead of the abnormality determination unit 413 illustrated in FIG. 22. In the fifth embodiment, the abnormality determination unit 511 includes an elastic fiber continuity determination unit 511a and a determination unit 511b. The elastic fiber continuity determination unit 511a determines whether the elastic fiber extracted from the fluorescence observation image by the elastic fiber extraction unit 412 has the continuity or not. The determination unit 511b determines whether there is abnormality in the blood vessel including the elastic fiber on the basis of the determination result made by the elastic fiber continuity determination unit 511a.

Here, that the elastic fiber has the continuity refers to the fact that the region extracted as the elastic fiber becomes annular without discontinuation, and is determined by the area of the elastic fiber region (hereinafter referred to as "area of region") and the circularity.

Figure 29:
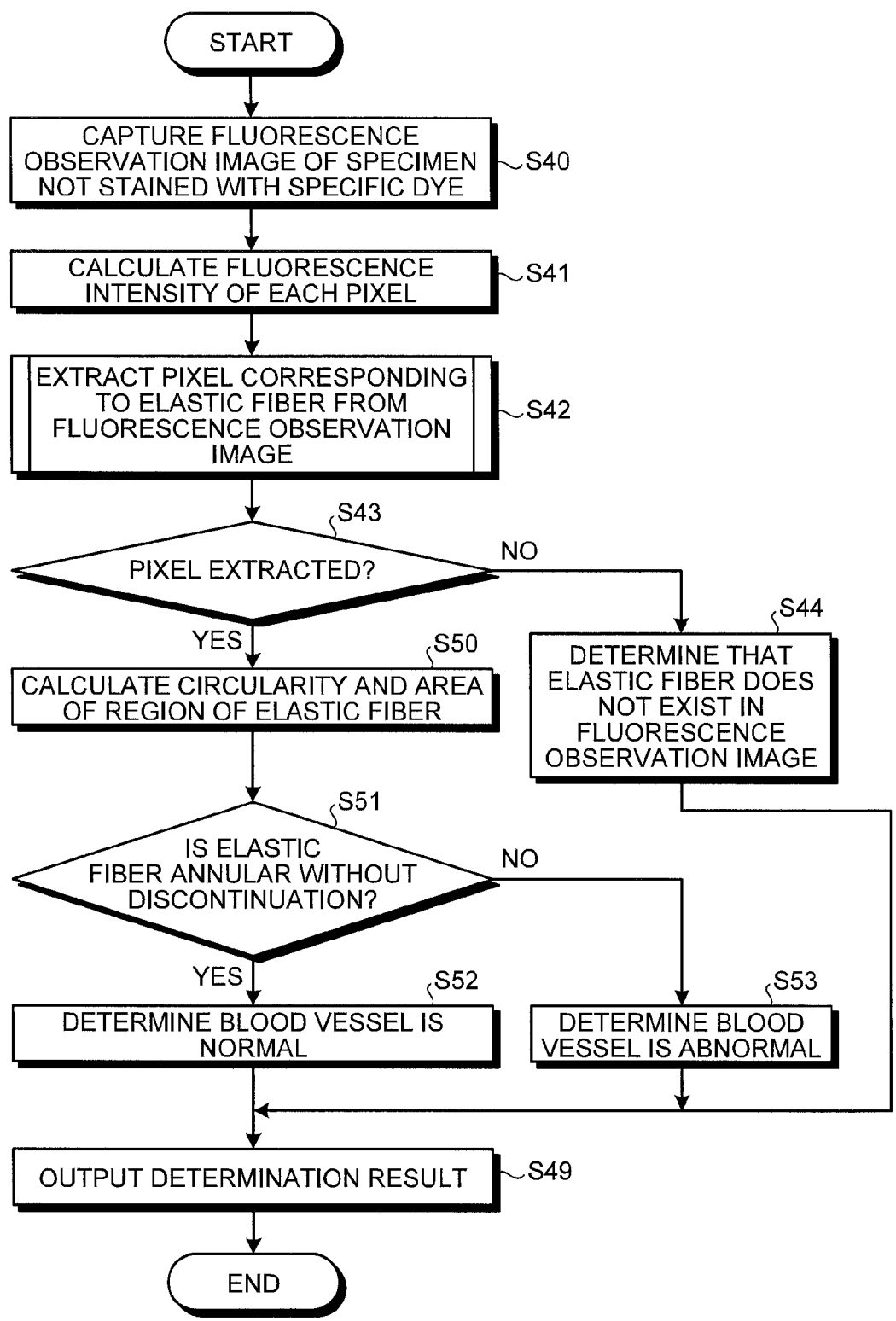
FIG. 29 is a flowchart illustrating a specimen observation method according to the fifth embodiment of the present invention.

Next, an image processing method according to the fifth embodiment is described. FIG. 29 is a flowchart illustrating a specimen observation method including the image processing method according to the fifth embodiment. Note that Steps S40 to S44 illustrated in FIG. 29 are similar to those of the fourth embodiment.

If it has been determined that the pixel representing the elastic fiber is extracted in Step S43 (Yes in Step S43), the elastic fiber continuity determination unit 511a calculates the area of region and the circularity of the pixel region extracted in Step S42 by, for example, Blob analysis (Step S50). Here, the Blob analysis refers to the image processing for analyzing the feature of the shape, such as the presence or absence, the number, the area, the length, the circumferential length, and the circularity of blobs, the blob referring to any of binary values (white and black) in a binary image obtained by binarizing the image to be processed.

In the subsequent Step S51, the elastic fiber continuity determination unit 511a determines whether the elastic fiber is annular without discontinuation on the basis of the area of region and the circularity of the elastic fiber. In this determination, various known techniques can be employed. In the fifth embodiment, for example, whether the area of region is greater than or equal to a specified threshold or the circularity is greater than or equal to a specified threshold is determined relative to each pixel region extracted in Step S42. If the area of region is greater than or equal to the specified threshold and the circularity is greater than or equal to the specified threshold, the elastic fiber is determined as being annular without discontinuation. On the other hand, if the area of region is less than the specified threshold and the circularity is less than the specified threshold, the elastic fiber is determined as being discontinuous.

In the case where the elastic fiber is annular without discontinuation (Yes in Step S51), the determination unit 511b determines that the blood vessel including the elastic fiber is normal (Step S52). On the other hand, in the case where the elastic fiber is discontinuous (No in Step S51), the determination unit 413b determines that the blood vessel including the elastic fiber is abnormal (Step S53). The subsequent Step S49 is similar to that of the fourth embodiment.

Next, a specific example of the image processing method according to the fifth embodiment is described. In the example below, the analysis was conducted using "Image J", the open-source image processing software developed by National Institutes of Health.

Figure 30A:
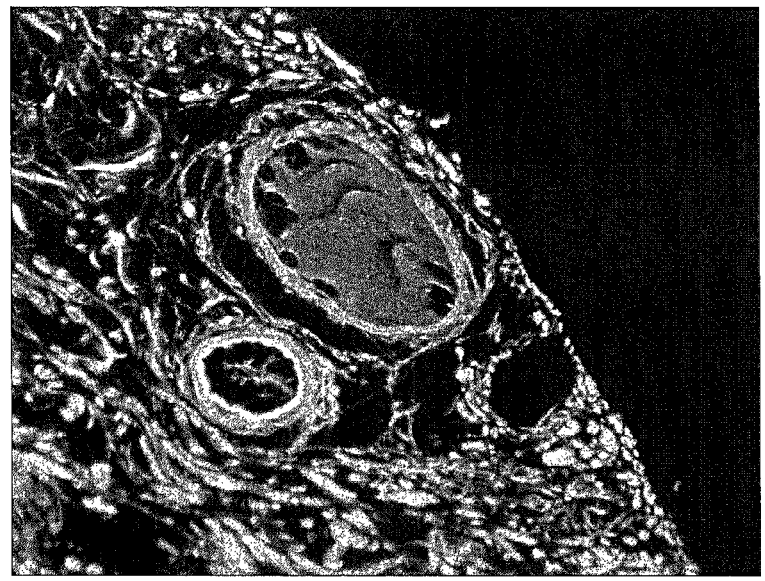
FIG. 30A is the fluorescence observation image in which the fluorescence is emitted by exciting the unstained specimen of the normal human colon with the UV ray.
Figure 30B:
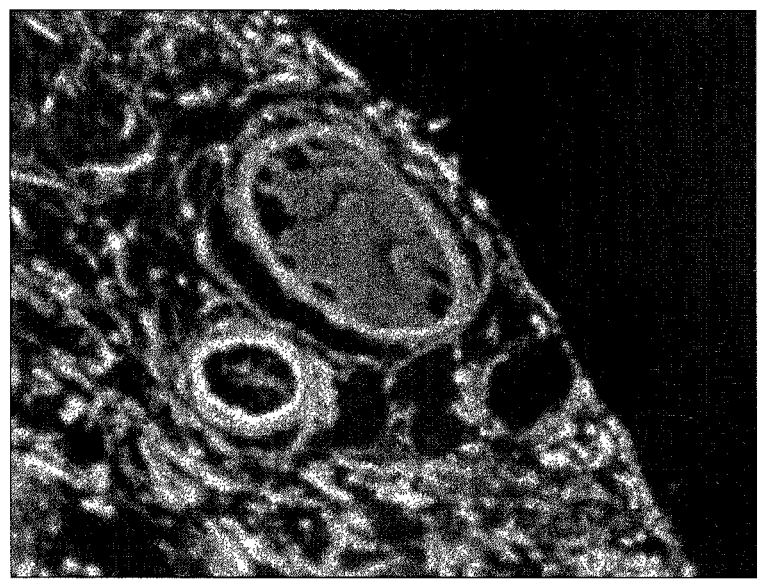
FIG. 30B is an image obtained by performing Gaussian filtering on the fluorescence observation image illustrated in FIG. 30A.

FIG. 30A is the fluorescence observation image in which the fluorescence is emitted by exciting the unstained specimen of the normal human colon with the UV ray. This fluorescence observation image was subjected to the Gaussian filtering (see FIG. 30B) and further to the binarizing process (see FIG. 30C). The region where the pixel value is zero in FIG. 30C (i.e., the black region) corresponds to the region with high fluorescence intensity in FIG. 30A, that is, the region of the pixel representing the elastic fiber.

Figure 30C:
FIG. 30C is an image obtained by binarizing the image illustrated in FIG. 30B.
Figure 30D:
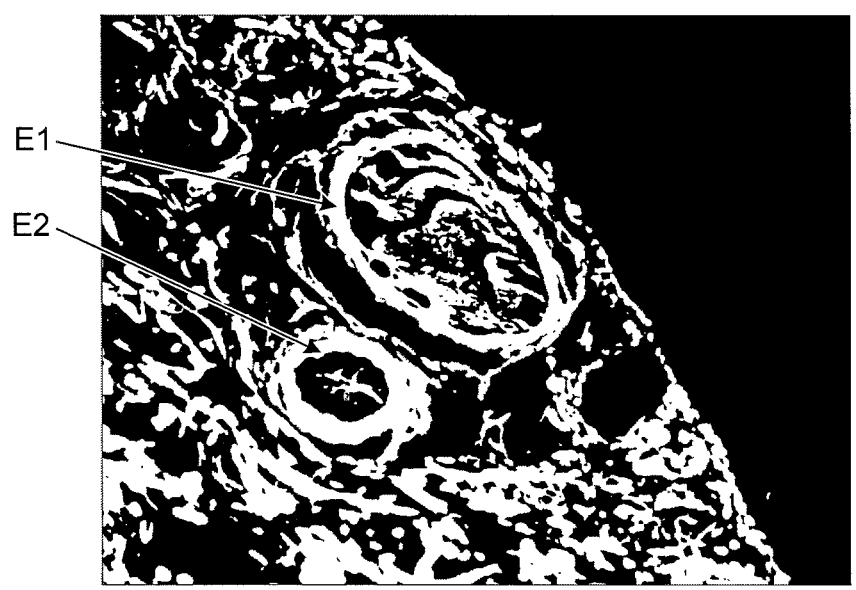
FIG. 30D is an image representing the results obtained by extracting the continuous elastic fiber through the blob analysis from the image illustrated in FIG. 30C.

The image illustrated in FIG. 30C was subjected to the process of extracting the continuous elastic fiber by the Blob analysis (the process of analyzing particles in "Image J"). On this occasion, the threshold of the area of region was set to 7000 and the threshold of the circularity was set to 0.02 in the extraction condition. In this case, the pixel region where the number of pixels is 7000 pixels or more and the circularity is 0.02 to 1 is extracted as the continuous elastic fiber. FIG. 30D is the image representing the result. As illustrated in FIG. 30D, the continuous elastic fibers E1 and E2, i.e., the normal blood vessel was able to be extracted from two positions in the image.

Figure 31A:
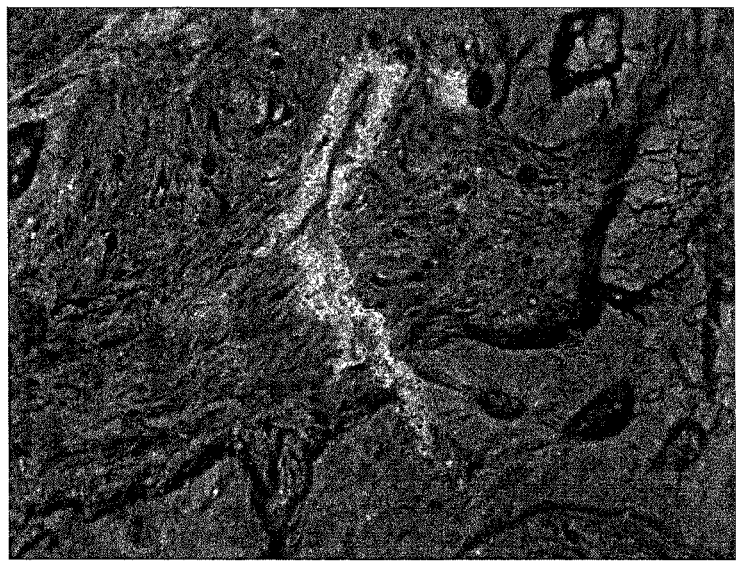
FIG. 31A is the fluorescence observation image in which the fluorescence is emitted by exciting the unstained specimen of the colon cancer with the UV ray.
Figure 31B:
FIG. 31B is an image obtained by performing Gaussian filtering on the fluorescence observation image illustrated in FIG. 31A.

FIG. 31A is the fluorescence observation image in which the fluorescence is emitted by exciting the unstained specimen of the colon cancer with the UV ray. This fluorescence observation image was subjected to the Gaussian filtering (see FIG. 31B) and further to the binarizing process (see FIG. 31C). The region where the pixel value is zero in FIG. 31C (i.e., the black region) corresponds to the region with high fluorescence intensity in FIG. 31A, that is, the region of the pixel representing the elastic fiber.

Figure 31C:
FIG. 31C is an image obtained by binarizing the image illustrated in FIG. 31A.
Figure 31D:
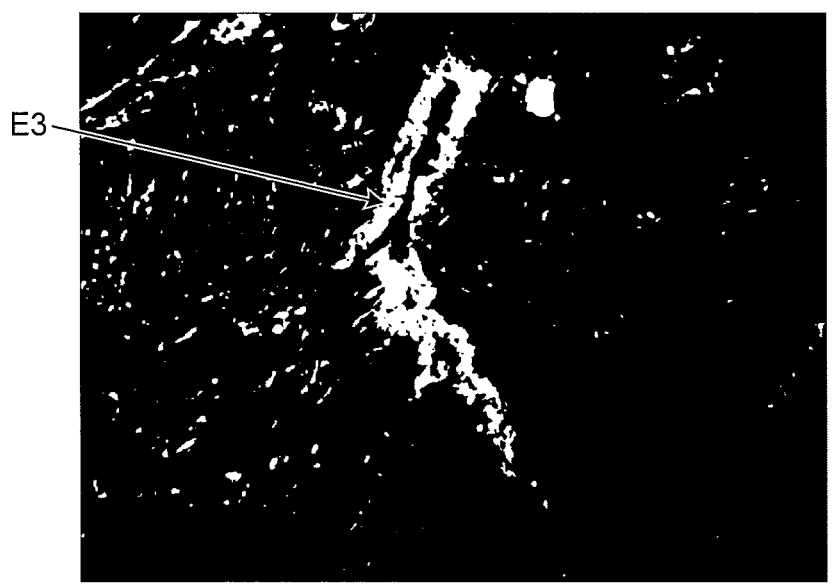
FIG. 31D is an image representing the results obtained by extracting the continuous elastic fiber through the blob analysis from the image illustrated in FIG. 31C.

The image illustrated in FIG. 31C was subjected to the process of extracting the elastic fiber through the blob analysis under the condition where the area of region is 7000 or more and the circularity is 0.02 to 1. FIG. 31D is the image representing the result. As illustrated in FIG. 31D, the continuous elastic fiber was not extracted from the image. In other words, the region in the fluorescence observation image (see FIG. 31A) corresponding to the elastic fiber E3 illustrated in FIG. 31D can be determined as the abnormal blood vessel with the vascular invasion.

As described above, the elastic fiber forming the blood vessel can be extracted by detecting the autofluorescence emitted from the specimen that is not stained or is stained with HE, and the presence or absence of the abnormality in the blood vessel can be estimated automatically by determining the continuity of the elastic fiber. Therefore, the accurate and stable diagnosis support for the blood vessel can be conducted without the human labor.

Sixth Embodiment

Figure 32:
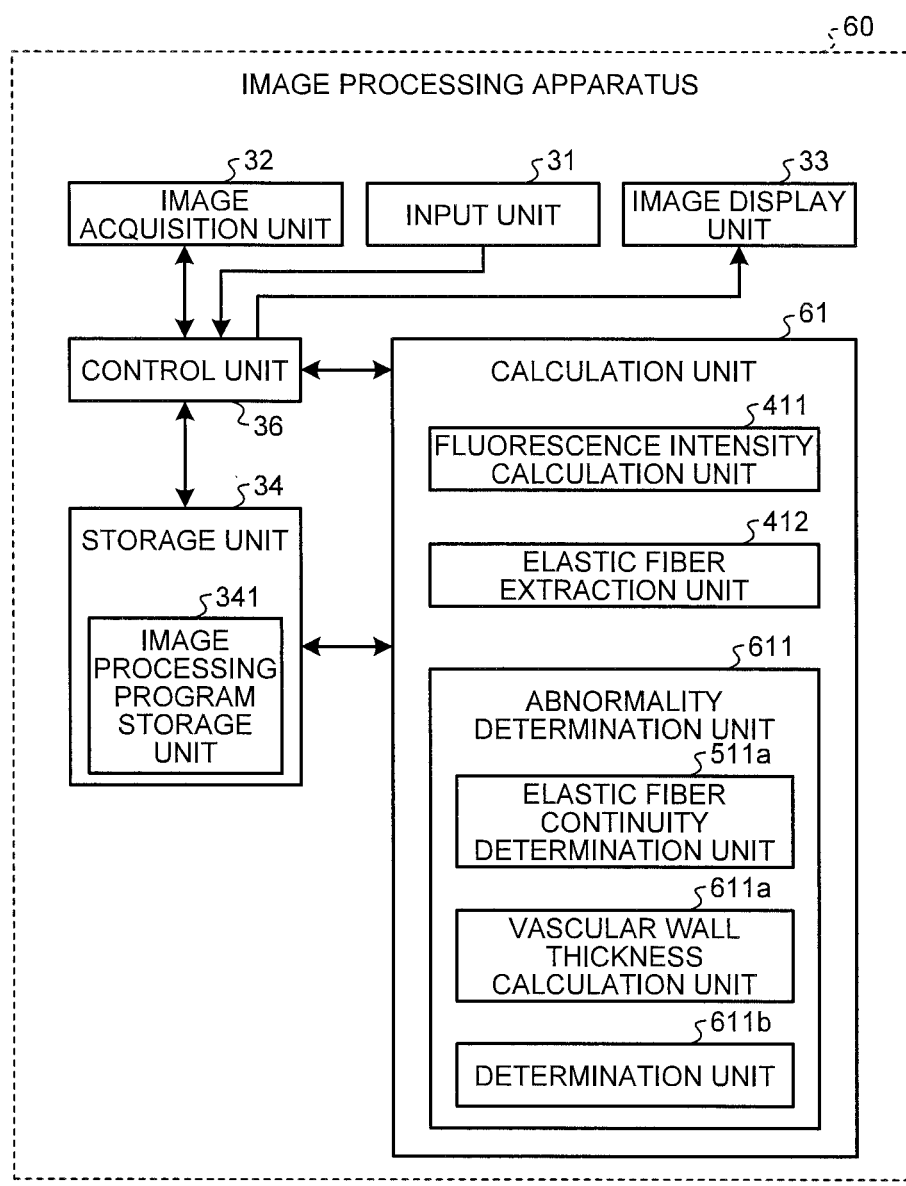
FIG. 32 is a block diagram illustrating a structure of an image processing apparatus according to a sixth embodiment of the present invention.

Next, a sixth embodiment of the present invention is described. FIG. 32 is a block diagram illustrating a structure of an image processing apparatus according to the sixth embodiment. A microscope system according to the sixth embodiment includes an image processing apparatus 60 having a calculation unit 61 instead of the image processing apparatus 30 illustrated in FIG. 1. The structure and the operation of the microscope device 10 and the imaging unit 20 and the structure and the operation of the units of the image processing apparatus 60 other than the calculation unit 61 are similar to those of the fourth embodiment.

The calculation unit 61 includes an abnormality determination unit 611 instead of the abnormality determination unit 413 illustrated in FIG. 22. In the sixth embodiment, the abnormality determination unit 611 includes the elastic fiber continuity determination unit 511*a*, a vascular wall thickness calculation unit 611*a*, and a determination unit 611*b*. The vascular wall thickness calculation unit 611*a* calculates the thickness of the vascular wall of the blood vessel including the elastic fiber that has been determined as having the continuity by the elastic fiber continuity determination unit 511*a*. The determination unit 611*b* determines whether the blood vessel is abnormal or not on the basis of the calculated thickness of the vascular wall.

Figure 33:
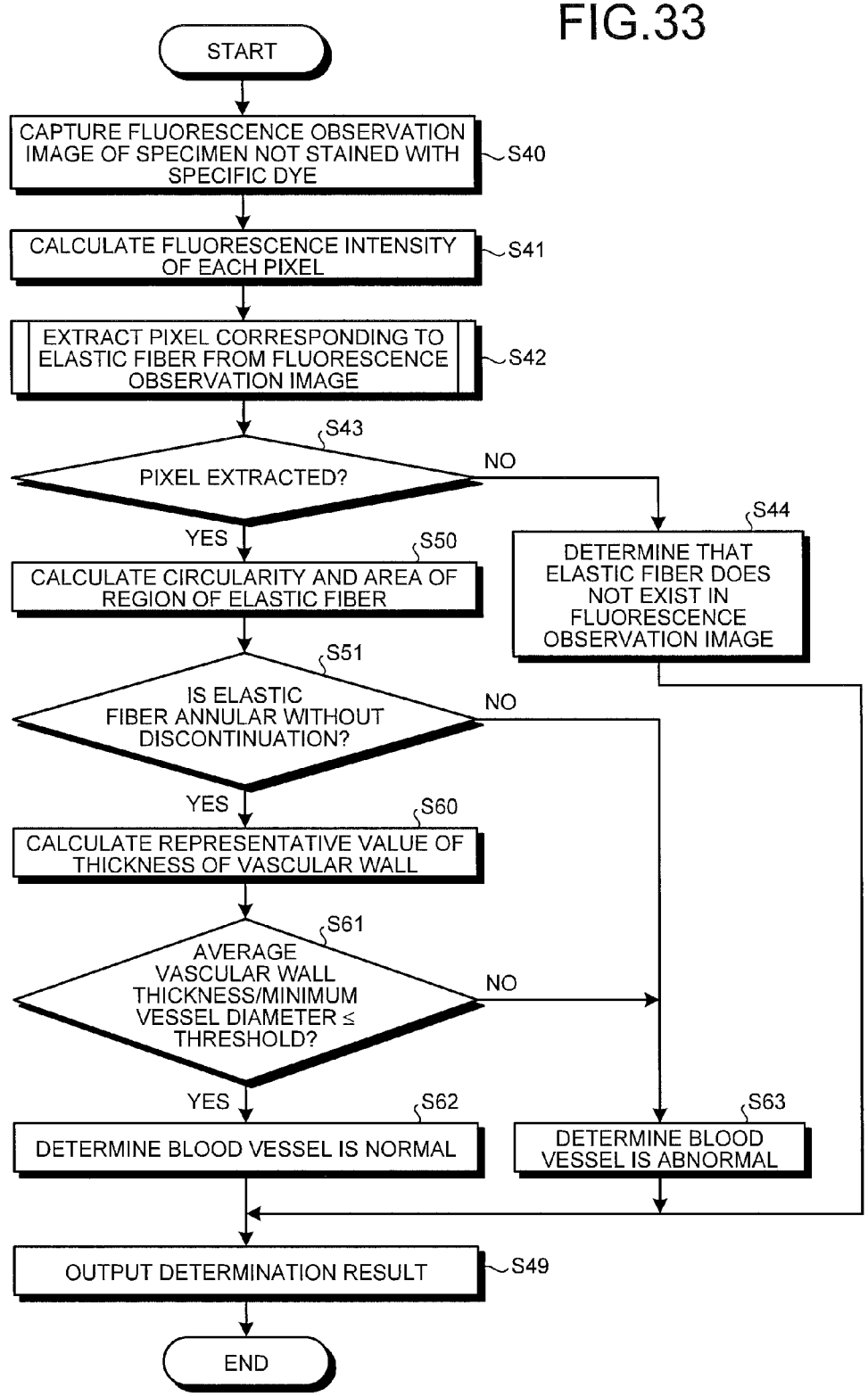
FIG. 33 is a flowchart illustrating a specimen observation method according to the sixth embodiment of the present invention.

Next, the image processing method of the sixth embodiment is described. FIG. 33 is a flowchart illustrating a specimen observation method including the image processing method according to the sixth embodiment. Note that Steps S40 to S44 and S50 and S51 illustrated in FIG. 33 are similar to those of the fifth embodiment.

Figure 34A:
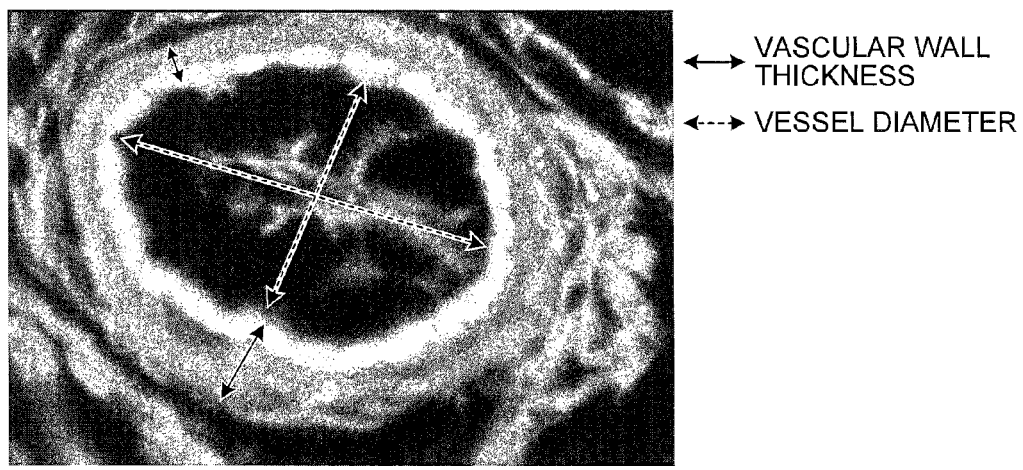
FIG. 34A is the image representing the vascular wall thickness and the vessel diameter of the blood vessel.

If it has been determined that the elastic fiber is annular without discontinuation in Step S51 (Yes in Step S51), the vascular wall thickness calculation unit 611*a* measures the thickness of the vascular wall (vascular wall thickness) of the blood vessel including the elastic fiber (see FIG. 34A), and calculates the representative value of the vascular wall thickness (Step S60). More specifically, the vascular wall thickness calculation unit 611*a* measures the outer diameter of the blood vessel based on the elastic fiber region by the blob analysis, and moreover measures the inner diameter of the blood vessel by extracting the region inside the elastic fiber corresponding to the inside of the blood vessel. Then, by calculating the difference between the outer diameter and the inner diameter, the vascular wall thickness can be obtained. In the sixth embodiment, the average value (average vascular wall thickness) is calculated as the representative value of the vascular wall thickness. Note that FIG. 34A is the image obtained by magnifying the portion of the fluorescence observation image (FIG. 30A) corresponding to the region including the elastic fiber E2 illustrated in FIG. 30D.

Figure 34B:
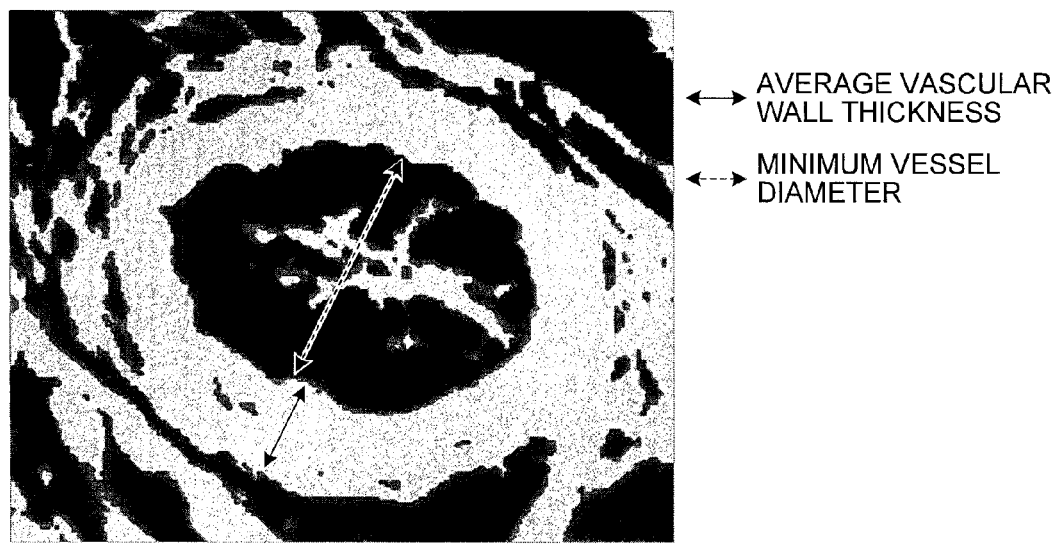
FIG. 34B is the image representing the average vascular wall thickness and the minimum vessel diameter of the blood vessel.

In the subsequent Step S61, the determination unit 611*b* determines whether the ratio of the average vascular wall thickness to the minimum value of the inner diameter of the blood vessel (vessel diameter), (average vascular wall thickness/minimum vessel diameter), is less than or equal to a specified threshold (see FIG. 34B). Note that FIG. 34B is the image obtained by performing threshold processing on the image of FIG. 34A based on the fluorescence intensity. Here, the average vascular wall thickness/minimum vessel diameter is the evaluation value in regard to the vascular wall thickness, and represents that as the value is increased, the blood vessel is crushed more to be flatter, in which case it is highly likely that the abnormality is determined.

If the average vascular wall thickness/minimum vessel diameter is less than or equal to the threshold (Yes in Step S61), the determination unit 611*b* determines that the blood vessel is normal (Step S62).

On the other hand, if it has been determined that the elastic fiber is discontinuous in Step S51 (No in Step S51) or that the average vascular wall thickness/minimum vessel diameter is larger than the threshold in Step S61 (No in Step S61), the determination unit 611*b* determines that the blood vessel is abnormal (Step S63). The subsequent Step S49 is similar to that of the fourth embodiment.

Next, a specific example of the image processing method according to the sixth embodiment is described. In the example below, the analysis was conducted using "Image J" in a manner similar to the fifth embodiment.

As a result of measuring the outer diameter of the elastic fibers E1 and E2 (see FIG. 30D) that have been determined as being annular without discontinuation in Step S51 through the blob analysis, the following results were obtained.
Elastic Fiber E1
Maximum vessel diameter (outer diameter): 519 pixels
Minimum vessel diameter (outer diameter): 309 pixels
Elastic Fiber E2
Maximum vessel diameter (outer diameter): 307 pixels
Minimum vessel diameter (outer diameter): 210 pixels As a result of performing the various measurements at the position of the minimum vessel diameter of each elastic fiber of E1 and E2 and the determination in Step S61, the following results were obtained. Note that the threshold in the determination is set to 40%.

Elastic Fiber E1
Outer diameter of vessel: 309 pixels
Inner diameter of vessel: 230 pixels
Vascular wall thickness: 79 pixels
Average vascular wall thickness/minimum vessel diameter (%):

$$(79/230) \times 100 = 34.3\%$$

Determination result: normal
Elastic Fiber E2
Outer diameter of vessel: 210 pixels
Inner diameter of vessel: 191 pixels
Vascular wall thickness: 19 pixels
Average vascular wall thickness/minimum vessel diameter (%):

$$(19/191) \times 100 = 9.9\%$$

Determination result: normal

As described above, according to the sixth embodiment, the elastic fiber forming the blood vessel is extracted by detecting the autofluorescence generated from the specimen that is not stained or is stained with HE, and the vascular wall thickness is evaluated by calculating the vascular wall thickness as well as determining the continuity of the elastic fiber, thereby estimating the presence or absence of the abnormality in the blood vessel automatically. Therefore, the accurate and stable diagnosis support for the blood vessel can be conducted without the human labor.

Seventh Embodiment

Figure 35:
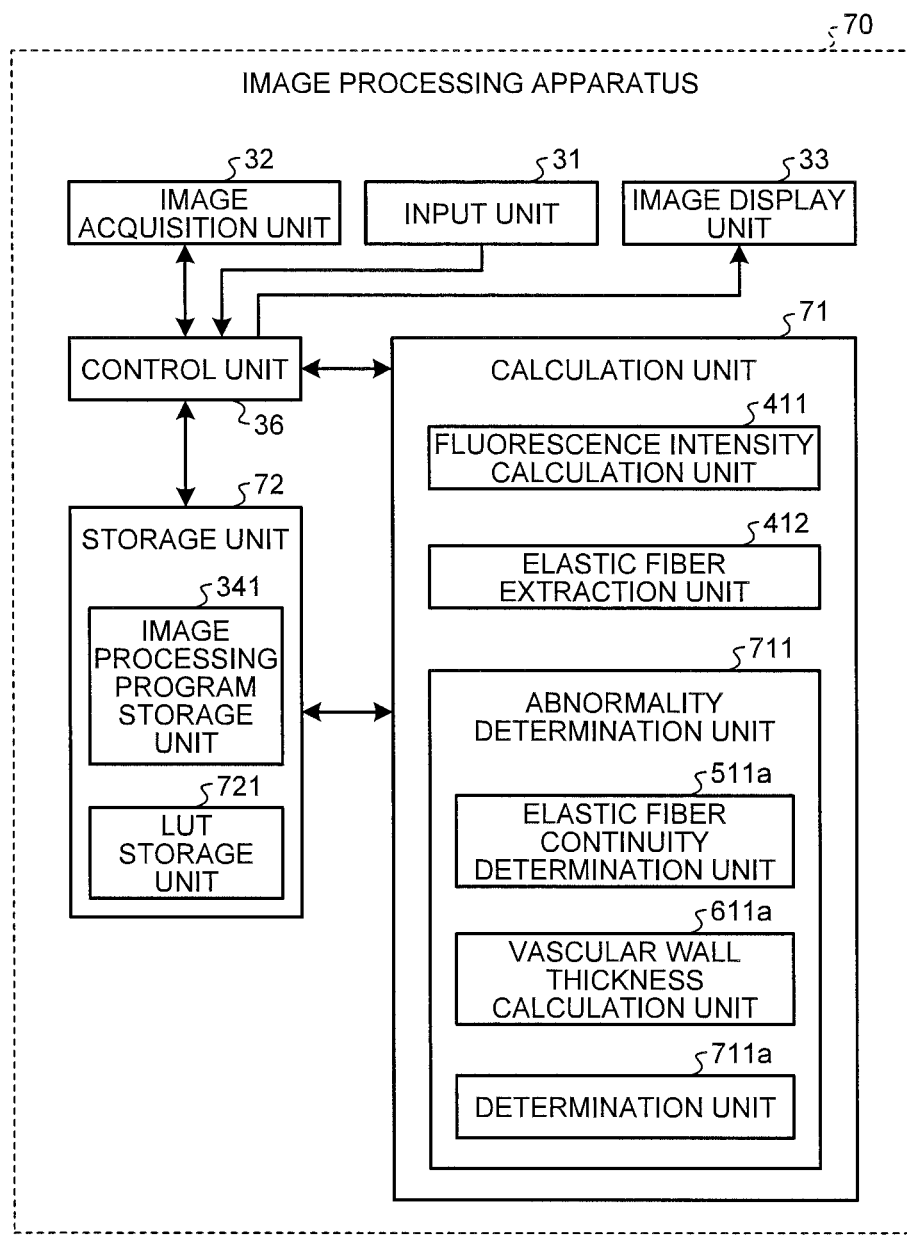
FIG. 35 is a block diagram illustrating a structure of an image processing apparatus according to a seventh embodiment of the present invention.

Next, a seventh embodiment of the present invention is described. FIG. 35 is a block diagram illustrating a structure of an image processing apparatus according to the seventh embodiment. A microscope system according to the seventh embodiment includes an image processing apparatus 70 illustrated in FIG. 35 instead of the image processing apparatus 30 illustrated in FIG. 1. The image processing apparatus 70 includes a calculation unit 71 and a storage unit 72 instead of the calculation unit 61 and the storage unit 34 illustrated in FIG. 32. The structure and the operation of the microscope device 10 and the imaging unit 20 and the structure and the operation of the units of the image processing apparatus 70 other than the calculation unit 71 and the storage unit 72 are similar to those of the sixth embodiment.

The calculation unit 71 includes an abnormality determination unit 711 instead of the abnormality determination unit 611 illustrated in FIG. 32. In the seventh embodiment, the abnormality determination unit 711 includes the elastic fiber continuity determination unit 511a, the vascular wall thickness calculation unit 611a, and a determination unit 711a. Among these, the operation of the elastic fiber continuity determination unit 511a and the vascular wall thickness calculation unit 611a is similar to that of the sixth embodiment.

The determination unit 711a determines whether there is abnormality in the blood vessel including the elastic fiber on the basis of the vascular wall thickness/vessel diameter ratio calculated by the vascular wall thickness calculation unit 611a and the circularity calculated by the elastic fiber continuity determination unit 511a, and moreover determines the risk level of the pathological condition or the like with reference to a lookup table stored in the storage unit 72 to be described below.

The storage unit 72 includes a lookup table (LUT) storage unit 721 in addition to the image processing program storage unit 341. FIG. 36A to FIG. 38B illustrate the lookup tables stored in the LUT storage unit 721.

A lookup table T11 illustrated in FIG. 36A is formed by correlating the circularity of the elastic fiber and the risk of pathological condition. A lookup table T12 illustrated in FIG. 36B is formed by correlating the ratio of the average vascular wall thickness to the minimum vessel diameter (hereinafter, vascular wall thickness/vessel diameter ratio) and the risk of pathological condition. The risk of pathological condition becomes higher as the circularity becomes smaller or as the vascular wall thickness/vessel diameter ratio becomes larger.

A lookup table T21 illustrated in FIG. 37A is formed by correlating the circularity of the elastic fiber and the risk of the arteriosclerosis. A lookup table T22 illustrated in FIG. 37B is formed by correlating the vascular wall thickness/vessel diameter ratio and the risk of the arteriosclerosis. The risk of the arteriosclerosis becomes higher as the circularity becomes smaller or as the vascular wall thickness/vessel diameter ratio becomes larger.

A lookup table T31 illustrated in FIG. 38A is formed by correlating the circularity of the elastic fiber and the risk of cancer infiltration. A lookup table T32 illustrated in FIG. 38B is formed by correlating the vascular wall thickness/vessel diameter ratio and the risk of cancer infiltration. The risk of cancer infiltration becomes higher as the circularity becomes smaller or as the vascular wall thickness/vessel diameter ratio becomes larger. Note that the specific numerals illustrated in FIG. 36A to FIG. 38B are mere examples.

Figure 39:
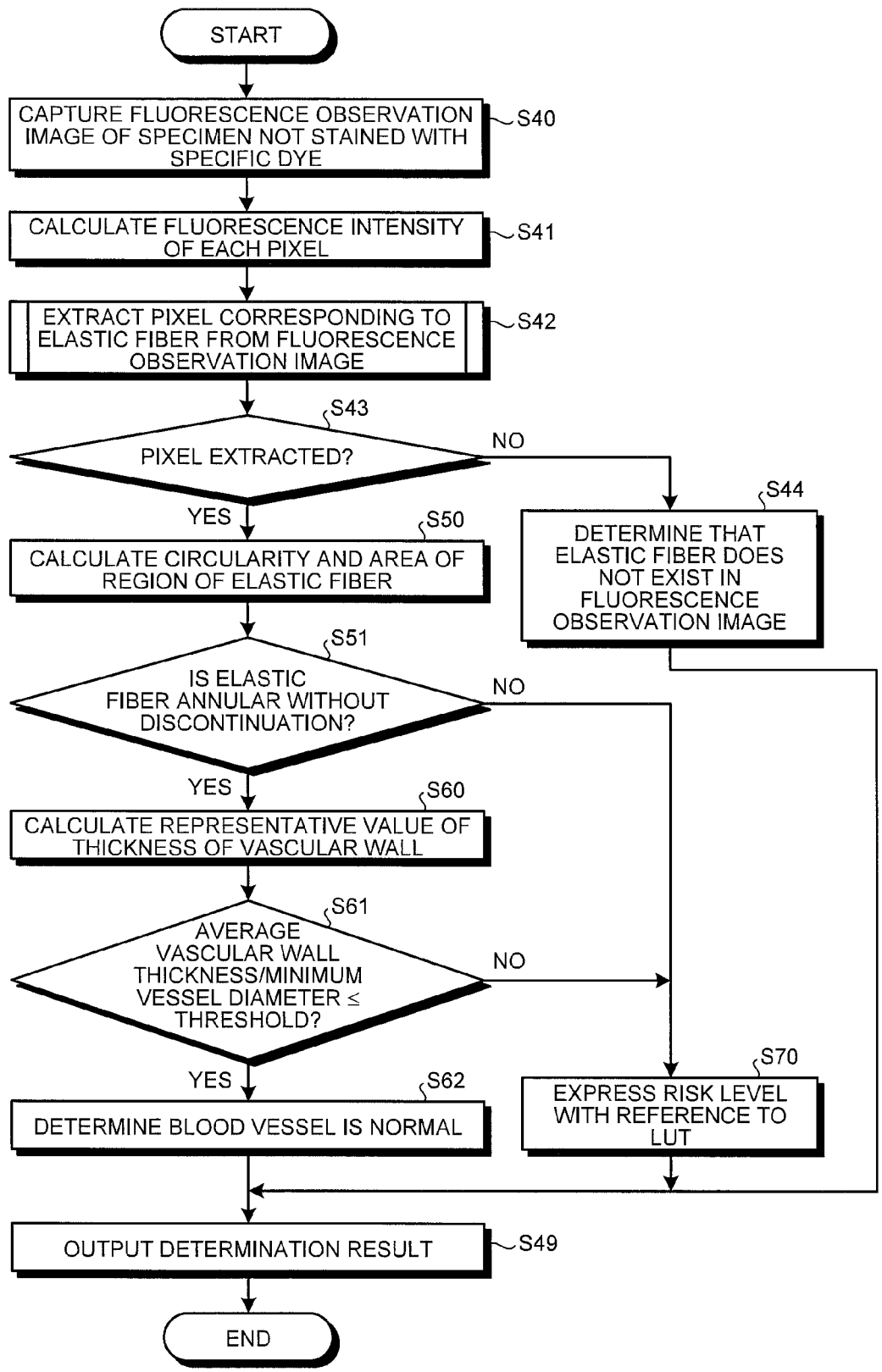
FIG. 39 is a flowchart illustrating a specimen observation method according to the seventh embodiment of the present invention.

Next, an image processing method according to the seventh embodiment is described. FIG. 39 is a flowchart illustrating a specimen observation method including the image processing method according to the seventh embodiment. Note that Steps S40 to S44, S50 and S51, and S60 to S62 illustrated in FIG. 39 are similar to those of the fifth embodiment.

If it has been determined that the elastic fiber is discontinuous in Step S51 (No in Step S51) or that the average vascular wall thickness/minimum vessel diameter is larger than the threshold in Step S61 (No in Step S61), the determination unit 711a returns the risk level according to the circularity of the elastic fiber and the vascular wall thickness/vessel diameter ratio with reference to the lookup tables T11 to T32 (Step S70). On this occasion, the lookup tables T11 and T12 are referred to for the risk in the pathological condition, the lookup tables T21 and T22 are referred to for the arteriosclerosis risk, and the lookup tables T31 and T32 are referred to for the cancer infiltration risk.

In the subsequent Step S49, the calculation unit 71 outputs the results of determination made by the determination unit 711a and the levels of the risk in the pathological condition, the arteriosclerosis risk, and the cancer infiltration risk, and displays the results on the image display unit 33 and stores the data in the storage unit 34. If the determination results of the risks based on the circularity and the determination results based on the vascular wall thickness/vessel diameter ratio are different, the both determination results may be displayed or one of them (for example, the one with the higher risk) may be output. Alternatively, the average value of the levels of the risks may be output. After that, the calculation unit 71 ends the process for the fluorescence observation image.

As described above, according to the seventh embodiment, the detailed diagnosis information related to the abnormality in the blood vessel can be acquired by referring to the lookup tables. Therefore, the accurate and specific diagnosis support for the blood vessel can be conducted stably without the human labor.

Figures 40, 41:
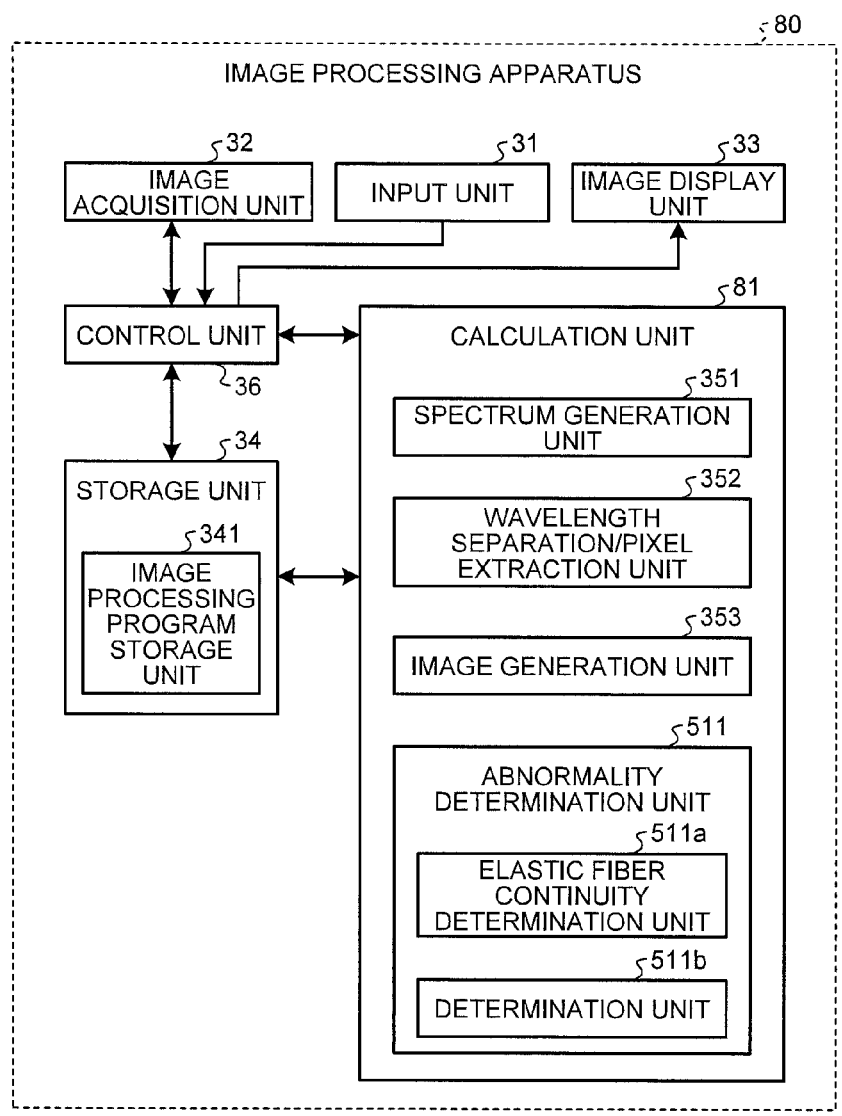
FIG. 40 is a lookup table in which the degree of continuity of the elastic fiber and the level of abnormality in the blood vessel are correlated to each other.
FIG. 41 is a block diagram illustrating a structure of an image processing apparatus according to an eighth embodiment of the present invention.

The determination for the abnormality in the blood vessel based on the lookup table described above may be applied to the fourth or fifth embodiment. For example, in the fourth embodiment, the presence or absence of, or the degree of the abnormality (the risk in the pathological condition, the arteriosclerosis risk, and the cancer infiltration risk) based on the morphological feature data of the blood vessel (for example, circularity) may be determined with reference to the lookup table stored in the storage unit in advance. Alternatively, in the fifth embodiment, the presence or absence of, or the degree of the abnormality of the blood vessel based on the presence or absence of, or the degree of the continuity of the elastic fiber may be determined with reference to the lookup table stored in the storage unit in advance. Specifically, if it has been determined that the elastic fiber is discontinuous in Step S51 illustrated in FIG. 29 (No in Step S51), the area of region of the elastic fiber (number of pixels) and the length of the contour of the elastic fiber (number of pixels on the circumferential length) are measured through the blob analysis and the ratio between the area of region and the length of the contour is obtained as the degree of continuity; thus, the abnormality of the blood vessel according to the degree of the continuity is determined with reference to the lookup table as illustrated in FIG. 40.

Eighth Embodiment

Next, an eighth embodiment of the present invention is described. FIG. 41 is a block diagram illustrating a structure of an image processing apparatus according to the eighth embodiment. A microscope system according to the eighth embodiment includes an image processing apparatus 80 illustrated in FIG. 41 instead of the image processing apparatus 30 illustrated in FIG. 1. The structure and the operation of the microscope device 10 and the imaging unit 20 are similar to those of the first embodiment.

In the fourth to seventh embodiments, the pixels representing the elastic fiber are extracted based on the fluorescence intensity in the fluorescence observation image of the specimen that is not stained or is stained with HE. However, the pixels representing the elastic fiber can be extracted based on the spectrum waveform of the fluorescence intensity in each pixel of the fluorescence observation image in a manner similar to the first embodiment.

As illustrated in FIG. 41, the image processing apparatus 80 includes a calculation unit 81 in which an abnormality determination unit 511 is further added to the calculation unit 35 illustrated in FIG. 1. In the calculation unit 81, the wavelength separation/pixel extraction unit 352 determines whether the peak wavelength and the waveform of the fluorescence intensity spectrum coincide with those of the spectrum of the elastic fiber for each pixel in the fluorescence observation image, and further determines whether the fluorescence intensity is greater than or equal to a specified threshold at the peak wavelength. Thus, the pixel representing the elastic fiber is extracted after being separated from the pixel representing the other specimen components (such as the blood corpuscle) in the fluorescence observation image. The abnormality determination unit 511 determines whether the blood vessel including the elastic fiber is abnormal or not on the basis of the elastic fiber extracted by the wavelength separation/pixel extraction unit 352. Note that the detailed operation of the abnormality determination unit 511 is similar to that of the fifth embodiment.

As described above, the pixel representing the elastic fiber is extracted based on the spectrum waveform of the fluorescence intensity from the fluorescence observation image of the specimen that is not stained or is stained with HE in the eighth embodiment; thus, the elastic fiber can be extracted more accurately. Therefore, the accuracy of the diagnosis support for the blood vessel can be improved further to enable the appropriate diagnosis support of the blood vessel.

As a modified example of the eighth embodiment, the abnormality determination unit 413 (see FIG. 22) for determining the abnormality of the blood vessel based on the morphological feature data of the blood vessel may be provided in a manner similar to the fourth embodiment, or the abnormality determination unit 611 (see FIG. 32) for determining the abnormality in the blood vessel based on the vascular wall thickness of the elastic fiber may be provided in a manner similar to the sixth embodiment. Further, the abnormality determination unit 711 (see FIG. 35) for estimating various risks with reference to the lookup table may be provided in a manner similar to the seventh embodiment.

The above fourth to eighth embodiments have described the image processing for the fluorescence observation image of the specimen that is not stained or is stained with HE. However, as long as the autofluorescence of the elastic fiber can be detected, the similar image processing is also applicable to the fluorescence observation image of the specimen stained with the dye for the bright-field observation other than the HE stain, such as the HDABNF stain (H: Hematoxylin, DAB: diaminobenzidine, NF: New Fuchsin), hematoxylin-DAB stain, hematoxylin-New Fuchsin stain, or hematoxylin single stain. The wavelength band and the imaging wavelength of the excitation light for each stained specimen, and the method of extracting the pixel representing the elastic fiber are as described in the third to fifth modified examples.

The first to eighth embodiments and the modified examples thereof described above are not limited to the description therein and various inventions can be made by combining as appropriate a plurality of elements disclosed in each embodiment and modified example. For example, some elements may be eliminated from the entire elements described in each embodiment. Alternatively, the components described in the different embodiments may be combined as appropriate.

(Note 1)

An image processing apparatus including:

an image acquisition unit that acquires image information representing a fluorescence observation image of a specimen that is not stained or is stained with hematoxylin-eosin;

a fluorescence intensity calculation unit that calculates, as fluorescence intensity, a value corresponding to intensity of fluorescence generated from the specimen based on the image information; and an abnormality determination unit that determines presence or absence of abnormality in a blood vessel in the fluorescence observation image based on the fluorescence intensity calculated by the fluorescence intensity calculation unit.

(Note 2)

The image processing apparatus according to note 1, wherein the abnormality determination unit includes:

a blood vessel feature data calculation unit that calculates morphological feature data of the blood vessel based on the fluorescence intensity; and a determination unit that determines the presence or absence of abnormality in the blood vessel based on the morphological feature data of the blood vessel.

(Note 3)

The image processing apparatus according to note 1, further including an elastic fiber extraction unit that extracts an elastic fiber from the fluorescence observation image based on the fluorescence intensity, wherein the abnormality determination unit includes:

an elastic fiber continuity determination unit that determines continuity of the elastic fiber; and a determination unit that determines the presence or absence of abnormality in the blood vessel based on a determination result of the continuity.

(Note 4)

The image processing apparatus according to note 3, wherein the elastic fiber continuity determination unit determines the continuity of the elastic fiber based on an area of a region surrounded by the elastic fiber and circularity of the elastic fiber.

(Note 5)

The image processing apparatus according to note 1, further including an elastic fiber extraction unit that extracts an elastic fiber from the fluorescence observation image based on the fluorescence intensity, wherein the abnormality determination unit includes:

a vascular wall thickness calculation unit that calculates a thickness of a vascular wall of the blood vessel based on the elastic fiber; and a determination unit that determines whether the blood vessel is normal or abnormal based on the thickness.

(Note 6)

The image processing apparatus according to note 5, wherein the vascular wall thickness calculation unit:

measures an outer diameter of the blood vessel based on the elastic fiber;

extracts a region inside the elastic fiber based on the elastic fiber;

measures an inner diameter of the blood vessel based on the region inside the elastic fiber; and calculates the thickness of the vascular wall based on the outer diameter and the inner diameter of the blood vessel.

(Note 7)

The image processing apparatus according to note 2, further including a storage unit that stores a lookup table in which the morphological feature data of the blood vessel are correlated with a determination result of the presence or absence of abnormality and/or a degree of abnormality in the blood vessel, wherein the determination unit determines the presence or absence of abnormality and/or the degree of abnormality with reference to the lookup table.

(Note 8)

The image processing apparatus according to note 3 or 4, further including a storage unit that stores a lookup table in which the determination result of the continuity of the elastic fiber is correlated with a determination result of the presence or absence of abnormality and/or a degree of abnormality in the blood vessel, wherein the determination unit determines the presence or absence of abnormality and/or the degree of abnormality with reference to the lookup table.

(Note 9)

The image processing apparatus according to note 5 or 6, further including a storage unit that stores a lookup table in which an evaluation value related to the thickness of the vascular wall is correlated with a determination result of the presence or absence of abnormality and/or a degree of abnormality in the blood vessel, wherein the determination unit determines the presence or absence of abnormality and/or the degree of abnormality with reference to the lookup table.

(Note 10)

The image processing apparatus according to any one of notes 1 to 9, further including a spectrum generation unit that generates a spectroscopic spectrum of each pixel in the fluorescence observation image, wherein the fluorescence intensity calculation unit calculates the fluorescence intensity with respect to a pixel region whose spectroscopic spectrum generated by the spectrum generation unit has a specified feature.

(Note 11)

The image processing apparatus according to note 10, wherein the fluorescence observation image is captured with excitation light with a wavelength band of 300 nm or more and 400 nm or less, and the fluorescence intensity calculation unit calculates the fluorescence intensity with respect to the pixel region with the spectroscopic spectrum having a peak wavelength of 560 nm.

(Note 12)

A microscope system including:

the image processing apparatus according to any one of notes 1 to 11;

a stage on which the specimen is configured to be placed;

an illumination optical system that emits excitation light toward the stage;

an objective optical system that is provided to face the stage and receives light from a direction of the specimen; and an imaging unit that generates image information by imaging observation light of the specimen transmitted through the objective optical system.

(Note 13)

The microscope system according to note 12, wherein the imaging unit includes a camera that is capable of capturing images in a plurality of different wavelength bands.

(Note 14)

An image processing method including:

an image acquisition step of acquiring image information representing an image acquired by irradiating a specimen that is not stained or is stained with hematoxylin-eosin with excitation light and by observing fluorescence generated from the specimen;

a fluorescence intensity calculation step of calculating, as fluorescence intensity, a value corresponding to intensity of the fluorescence generated from the specimen based on the image information; and an abnormality determination step of determining presence or absence of abnormality in a blood vessel in the image based on the fluorescence intensity calculated in the fluorescence intensity calculation step.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
an image acquisition unit that acquires image information representing a fluorescence observation image of a specimen stained with hematoxylin-eosin;
a spectrum generation unit that generates a plurality of spectra each representing a wavelength distribution of fluorescence intensity in a plurality of pixels in the fluorescence observation image;
a pixel extraction unit that extracts at least two pixel groups with a feature of a particular spectrum from the plurality of pixels, wherein the pixel extraction unit is configured to:
extract the at least two pixel groups with reference to at least two fluorescence intensity spectra acquired respectively in advance with respect to at least two kinds of components in the specimen;
extract pixel groups having the same peak wavelengths as those of the at least two fluorescence intensity spectra, as the at least two pixel groups, respectively;
extract a pixel group having a peak wavelength of 560 nm as a pixel group representing an elastic fiber in the specimen; and
extract a pixel group having a peak wavelength of 570 nm as a pixel group representing a blood corpuscle in the specimen;
an image generation unit that generates an image based on the extracted pixel groups; and
an abnormality determination unit that determines a presence or absence of abnormality in a blood vessel in the fluorescence observation image based on the pixel group representing the elastic fiber.

2. The image processing apparatus according to claim 1, wherein the pixel extraction unit extracts, as the pixel group representing the elastic fiber, a pixel group whose fluorescence intensity at a peak wavelength is greater than or equal to a specified threshold from among a plurality of pixels in the pixel group having a peak wavelength of 560 nm.

3. The image processing apparatus according to claim 1, wherein
the image acquisition unit further acquires second image information representing a bright-field observation image of the specimen stained with hematoxylin-eosin, and
the image generation unit further generates a second image based on the second image information.

4. The image processing apparatus according to claim 3, further comprising an image display unit that displays at least one of the image and the second image.

5. The image processing apparatus according to claim 3, further comprising an image synthesis unit that generates a synthesis image obtained by overlapping the image on the second image.

6. The image processing apparatus according to claim 5, further comprising an image display unit that displays at least one of the image, the second image, and the synthesis image.

7. The image processing apparatus according to claim 1, wherein the abnormality determination unit includes:
a blood vessel feature data calculation unit that calculates morphological feature data of a blood vessel based on the pixel group representing the elastic fiber; and
a determination unit that determines the presence or absence of abnormality in the blood vessel based on the morphological feature data of the blood vessel.

8. The image processing apparatus according to claim 1, wherein the abnormality determination unit includes:
an elastic fiber continuity determination unit that determines continuity of the elastic fiber; and
a determination unit that determines the presence or absence of abnormality in the blood vessel based on a determination result of the continuity.

9. The image processing apparatus according to claim 8, wherein the elastic fiber continuity determination unit determines the continuity of the elastic fiber based on an area of a region surrounded by the elastic fiber and circularity of the elastic fiber.

10. The image processing apparatus according to claim 1, wherein the abnormality determination unit includes:
a vascular wall thickness calculation unit that calculates a thickness of a vascular wall of the blood vessel based on the elastic fiber; and
a determination unit that determines whether the blood vessel is normal or abnormal based on the thickness.

11. The image processing apparatus according to claim 10, wherein the vascular wall thickness calculation unit:
measures an outer diameter of the blood vessel based on the elastic fiber;
extracts a region inside the elastic fiber based on the elastic fiber;
measures an inner diameter of the blood vessel based on the region inside the elastic fiber; and
calculates the thickness of the vascular wall based on the outer diameter and the inner diameter of the blood vessel.

12. The image processing apparatus according to claim 7, further comprising a storage unit that stores a lookup table in which the morphological feature data of the blood vessel are correlated with a determination result of the presence or absence of abnormality and/or a degree of abnormality in the blood vessel, wherein
the determination unit determines the presence or absence of abnormality and/or the degree of abnormality with reference to the lookup table.

13. The image processing apparatus according to claim 8, further comprising a storage unit that stores a lookup table in which the determination result of the continuity of the elastic fiber is correlated with a determination result of the presence or absence of abnormality and/or a degree of abnormality in the blood vessel, wherein
the determination unit determines the presence or absence of abnormality and/or the degree of abnormality with reference to the lookup table.

14. The image processing apparatus according to claim 10, further comprising a storage unit that stores a lookup table in which an evaluation value related to the thickness of the vascular wall is correlated with a determination result of the presence or absence of abnormality and/or a degree of abnormality in the blood vessel, wherein
the determination unit determines the presence or absence of abnormality and/or the degree of abnormality with reference to the lookup table.

15. A microscope system comprising:
the image processing apparatus according to claim 1;
a stage on which the specimen is configured to be placed;
an epi-illumination optical system that emits excitation light toward the stage;

an objective optical system that is provided to face the stage and receives light from a direction of the specimen;

a filter that extracts fluorescence light from the light transmitted through the objective optical system; and an imaging unit that is provided on an optical path of the light transmitted through the objective optical system and generates image information by capturing an observation image of the specimen.

16. The microscope system according to claim 15, further comprising:

a transmission illumination optical system that emits illumination light toward the stage; and a switching unit that switches between the excitation light and the illumination light to be emitted toward the specimen, wherein the filter is provided removably on the optical path of the light transmitted through the objective optical system and extracts the fluorescence light with a specified wavelength band from the light.

17. The microscope system according to claim 15, wherein a wavelength band of the excitation light is 300 nm or more and 400 nm or less.

18. The microscope system according to claim 17, wherein the wavelength band of the fluorescence light is 520 nm or more and 650 nm or less.

19. The microscope system according to claim 15, wherein the imaging unit includes a camera that is capable of capturing images in a plurality of wavelength bands.

20. An image processing method comprising:

acquiring image information representing a fluorescence observation image of a specimen stained with hematoxylin-eosin;

generating a plurality of spectra each representing a wavelength distribution of fluorescence intensity in a plurality of pixels in the fluorescence observation image;

extracting at least two pixel groups with a feature of a particular spectrum from the plurality of pixels, wherein the extracting:

extracts the at least two pixel groups with reference to at least two fluorescence intensity spectra acquired respectively in advance with respect to at least two kinds of components in the specimen;

extracts pixel groups having the same peak wavelengths as those of the at least two fluorescence intensity spectra, as the at least two pixel groups, respectively;

extracts a pixel group having a peak wavelength of 560 nm as a pixel group representing an elastic fiber in the specimen; and extracts a pixel group having a peak wavelength of 570 nm as a pixel group representing a blood corpuscle in the specimen;

generating an image based on the extracted pixel groups; and determining a presence or absence of abnormality in a blood vessel in the fluorescence observation image based on the pixel group representing the elastic fiber.

* * * * *